US006875433B2

(12) United States Patent
Hart et al.

(10) Patent No.: US 6,875,433 B2
(45) Date of Patent: Apr. 5, 2005

(54) MONOCLONAL ANTIBODIES AND COMPLEMENTARITY-DETERMINING REGIONS BINDING TO EBOLA GLYCOPROTEIN

(75) Inventors: Mary Kate Hart, Frederick, MD (US); Julie Wilson, Birmingham, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 82 days.

(21) Appl. No.: 10/226,795

(22) Filed: Aug. 23, 2002

(65) Prior Publication Data

US 2004/0053865 A1 Mar. 18, 2004

(51) Int. Cl.$^7$ ................................................ A61K 39/42

(52) U.S. Cl. ................................ 424/159.1; 424/130.1; 530/300; 435/345

(58) Field of Search ........................... 424/159.1, 130.1; 435/91.1, 69.1, 345; 530/300

(56) References Cited

U.S. PATENT DOCUMENTS

| | | | | |
|---|---|---|---|---|
| 5,792,462 A | | 8/1998 | Johnston et al. | 424/199.1 |
| 5,977,316 A | * | 11/1999 | Chatterjee et al. | 530/387.2 |
| 6,340,463 B1 | | 1/2002 | Mitchell et al. | 424/263.1 |
| 6,630,144 B1 | * | 10/2003 | Hart et al. | 424/159.1 |
| 2003/0224015 A1 | | 12/2003 | Hart et al. | |
| 2004/0146859 A1 | | 7/2004 | Hart et al. | |

FOREIGN PATENT DOCUMENTS

| | | |
|---|---|---|
| WO | WO 96/37616 | 11/1996 |
| WO | WO 99/32147 | 7/1999 |
| WO | WO 00/00617 A2 | 1/2000 |
| WO | WO 01/016183 A1 * | 3/2001 |

OTHER PUBLICATIONS

Maruyama et al, Journal of Virology, Jul. 1999, vol. 73, No. 7, pp. 6024–6030.*

Wilson et al., "Vaccine Potential of Ebola Virus VP24, VP30, VP35 and VP40 Proteins", Virology 286, pp. 384–390 (2001).

Wilson and Hart, "Protection from Ebola Virus Mediated by Cytotoxic T Lymphocytes Specific for the Viral Nucleoprotein", Journal of Virology, Mar. 2001, vol. 75, No. 6, pp. 2660–2664.

Pushko et al., "Venezuelan Equine Encephalitis Virus Replicon Vector: Immunogenicity Studies with Ebola NP and GP Genes in Guinea Pigs", Vaccines 97, Molecular Approaches to the Control of Infectious Diseases, Cold Spring Harbor Laboratory Press, 1997, pp. 253–258.

Geisbert et al, "Evaluation in Nonhuman Primates of Vaccines Against Ebola Virus", Emerging Infectious Diseases, vol. 8, No. 5, May 2000, pp. 503–507.

Pushko et al., "Recombinant RNA Replicons Derived from Attenuated Venezuelan Equine Encephalitis Virus Protect Guinea Pigs and Mice from Ebola Hemorrhagic Fever Virus", JVAC, Vaccine, pp. 1–12.

Abstract, W33–5, Hooper et al., "DNA Vaccination Against Poxviruses Using Combinations ofIMV and EEV Immunogens", Jul. 2000, American Society for Virology Meeting.

Abstract, P23–6, Hooper et al., DNA Immunization with the Vaccinia L1R and/or A33R genes, Jul. 1998, Poster at American Soceity for Virology Meeting.

Meyer et al., "Identification of Binding Sites for Neutralizing Monoclonal Antibodies on the 14–kDa Fusion protein of Orthopox Viruses", Virology 200, pp. 778–783 (1994).

Czerny and Mahnel, "Structural and functional analysis of orthopoxvirus epitopes with neutralizing monoclonal antibocies", J. General Virology (1990), vol. 71, pp. 2341–2352.

Hooper et al., "DNA Vaccination with Vaccinia Virus L1R and A33R Genes Protects Mice Against a Lethal Poxvirus Challenge", Virology 266, pp. 329–339 (2000).

Vazquez and Esteban, "Identification of Functional Domains in the 14–Kilodalton Envelope Protein (A27L) of Vaccinia Virus", J. Virology, vol. 73, No. 11, Nov. 1999, pp. 9098–9109.

Vazquez et al., "The Vaccinia Virus 14–Kilodalton (A27L) Fusion Protein Forms a Triple Coiled–Coil Structure and Interacts with the 21–Kilodalton (A17L) Virus Membrane Protein through a C–Terminal alpha–Helix", J. Virology, vol. 72, No. 12, Dec. 1998), pp. 10126–10137.

Rodriguez et al., "The Vaccinia Virus 14–Kilodalton Fusion Protein Forms a Stable Complex with the Processed Protein Encoded bythe Vaccinia Virus A17L Gene", J. Virology, vol. 67, No. 6, Jun. 1993, pp. 3435–3440.

Lai et al., "The Purified 14–Kilodalton Envelope Protein of Vaccinia Virus Produced in *Escherichia coli* Induces Virus Immunity in Animals", J. Virology, vol. 65, No. 10, Oct. 1991, pp. 5631–5635.

Rodriguez and Esteban, "Mapping and Nucleotide Sequence ofthe Vaccinia Virus Gene That Encodes a 14–Kilodalton Fusion Proteins", J. Virology, Nov. 1987, vol. 61, No. 11, pp. 3550–3554.

Rodriguez et al., "Isolation and Characterization of Neutralizing Monoclonal Antibodies to Vaccinia Virus", J. Virology, Nov. 1985, vol. 56, No. 2, pp. 482–488.

(Continued)

*Primary Examiner*—Ali R. Salimi
(74) *Attorney, Agent, or Firm*—Elizabeth Arwine

(57) ABSTRACT

In this application are described Ebola GP monoclonal antibodies, epitopes recognized by these monoclonal antibodies, and the sequences of the variable regions of some of these antibodies. Also provided are mixtures of antibodies of the present invention, as well as methods of using individual antibodies or mixtures thereof for the detection, prevention, and/or therapeutical treatment of Ebola virus infections in vitro and in vivo.

6 Claims, 2 Drawing Sheets

OTHER PUBLICATIONS

PubMed Abstract from National Library of Medicine, of Sanderson et al., "The vaccinia virus A27L protein is needed forhte microtubule–dependent transport of intracellular mature virus particles", J. Gen. Virol., Jan. 2000; 81 pt 1:47–58.

PubMed Abstract from National Library of Medicine, of Rodriguez et al., "Isolation and Characterization of Neutralizing Monoclonal Antibodies to Vaccinia Virus", J. Virology, Nov. 1985, vol. 56, No. 2, pp. 482–488.

Lin et al., "Vaccinia virus envelope H3L protein binds to cell surface heparan sulfate and is important for intracellular mature virion morphogenesis and virus infection in vitro and in vivo", J. Virology, Apr. 2000, vol. 74, No. 7, pp. 3353–3365.

Gordon et al., "A Prominent Antigenic Surface Polypeptide Involved in the Biogenesis and Function of the Vaccinia Virus Envelope", Virology 181, pp. 671–686 (1991).

Ichihashi et al., "Identification of a Vaccinia Virus Penetration Protein", Virology 202, pp. 834–843 (1994).

Demkowicz et al., "Identification and Characterization of VAccinia Virus Genes Encoding Proteins That Are Highly Antigenic in Animals and Are Immunodominant in Vaccinated Humans", J. Virology, Jan. 1992, vol. 66, No. 1, pp. 386–398.

Wilson et al., "Ebola virus: the search for vaccines and treatments", CMLS Cell, Mol. Life, Sci., 58 (2001) pp. 1–16.

Geisbert et al., "Evaluation in Nonhuman Primates of Vaccines Against EbolA Virus", Emerging Infectious Diseases, vol. 8, No. 5, May 2002, 15 pages.

Volchkov et al., "The envelopa glycoprotein of Ebolavirus contains an immunosuppressive–like domain similar to oncogenic retroviruses", FEBS Letters, vol. 305, No. 3, Jul. 1992, pp. 181–184.

Ichihashi and Oie, "NeutralizingEpitope on Penetration Protein of Vaccinia Virus", Virology 220, 1996, pp. 491–494.1

Wolffe et al., "A Myristylated Membrane Protein Encoded by the Vaccinia Virus L1R Open Reading Frame is the Target of Potent Neutralizing Monoclonal Antibodies", Virology 211, 1995, pp. 53–63.

Roper et al., "Extracellular Vaccinia Virus Envelope Glycoprotein Encoded by the A33R Gene", J. Virology, Jun. 1996, vol. 70, No. 6, pp. 3753–3762.

Isaacs et al., "Characterization of a Vaccinia Virus–Encoded 42–Kilodalton Class I Membrane Glycoprotein Component of the Extracellular Virus Envelope", J. Virology, Dec. 1992, vol. 66, No. 12, pp. 7217–7224.

Sanchez et al., "Variation in the Glycoprotein nad VP35 Genes of Marburg Virus Strains", Virology 240, pp. 138–146 (1996).

Hevey et al., "Marburg Virus Vaccines Based upon Alphavirus Replicons Protect Guinea Pigs and Nonhumans Primates"Virology 251, pp. 28–37 (1998).

Bukreyev et al., "The VP35 and VP40 proteins of filoviruses," FEBS Letters, vol. 322, No. 1, May 1993, pp. 41–46.

Elliott et al., "Ebola protein analyses for the determination of genetic organization", Archives of Virology, 1993, vol. 133, pp. 423–436.

Gilligan et al., "Assessment of Protective Immunity Conferred by Recombinant Vaccinia Viruses to Guinea Pigs Challenged with Ebola Virus", Vaccines 97, 1997, pp. 87–92.

Hart et al., "Priming of anti–human immunodeficiency virus (HIV) CD8+ cytotoxic T cells in vivo by carrier–free HIV synthetic peptides", PNAS USA, vol. 88, Nov. 1991, pp. 9448–9452.

Nicolet and Paulnock, "Promoter Analysis of an Interferon–Inducible Gene Associated wit hmacrophage Activation", J. Immunology, 1994, pp. 152–162.

Vanderzanden et al., "DNA Vaccines Expressing either the GP or NP Genes of Ebola Virus Protect Mice from Lethal Challenge", Virology 246, pp. 134–144 (1998).

International Search Report issued is corresponding international patent application PCT/US03/27450, mailed Mar. 10, 2004 (7 pages).

Wilson et al., "Ebola Virus; the search for vaccines and treatments." CMLS Cellular and Molecular Life Sciences, Nov. 2001, vol. 58, pp. 1826–1841.

Maruyama et al., "Ebola Virus Can Be Effectively Neutralized by Antibody Produced in Natural Humand Infection." Journal of Virology, Jul. 1999, vol. 73, No. 7, pp. 6–24–6030.

Khaw, et al., "Technetium–99m Labeling of Antibodies to Cardiac Myosia Fab and to Human Fibrinogen", Radiochemistry and Radiopharmaceuticals, J. Nucl. Med., vol. 23, No. 11, pp. 1011–1019 (1982).

Farid and Linthicum, "Idiotypes, Paratopes, and Molecular Mimicry", pp. 1–5, and "An Idiotype Approach for a Vaccine Against Hepatitis B Surface Antigen", pp. 285–300, both in Anti–Idiotypes, Receptors, and Molecular Mimicry, Ivy Springer–Verlag, (1988).

Kabat et al., "Sequence of Proteins of Immunological Interest", vol. 1, Fifth Ed., pp. xiv–xix and 33 pages of sequences (1991).

Waldmann, "Manipulation of T–Cell Responses with Monoclonal Antibodies", Ann. Rev. Immunol. (1989) 7:407–44.

Schuurs and Van Weemen, Review: Enzyme–Immunoassay, Clinica Chimica Acta, 81 (1977) 1–40.

Kennedy et al., Review: Protein–Protein Coupling Reactions and the Applications of Protein Conjugates, Clinica Chimica Acta, 70 (1976) 1–31.

"Continuous cultures of fused cells secreting antibody of predefined specificity", Nature, vol. 256, pp. 495–497, Aug. 7, 1975.

Vokchkov et al., "Processing of the Ebola virus glycoprotein by the proprotein convertase furin", Proc.Natl.Acad. Sci.USA, vol. 95, pp. 5762–5767, May 1998.

Volchkov et al., "GP mRNA of Ebola Virus is Edited by the Ebola Virus Polymerase and T7 and Vaccinia Virus Polymerases" Virology 214, 421–430 (1995).

Stiles et al., "Production and characterization of monoclonal antibodies against NAJA NAJA ATRA cobrotoxin," Toxicon, vol. 29, No. 10, pp. 1195–1204, 1991.

Volchkov et al., "Release of viral glycoproteins during Ebola virus infection", Virology 245, 110–119 (1998).

Feldmann et al., "Marburg virus, a filevirus: messenger RNAs, gene order, and regulatory elements of the replication cycle", Virus Research, 24 (1992) 1–19.

Sanchez et al, "The nucleoprotein gene of Ebola virus: cloning, sequencing, and in vitro expression", Virology 170, 81–91 (1989).

Moe et al., "Plaque assay for Ebola virus", J. Clinical Microbiology, Apr. 1981, vol. 13, No. 4, pp. 791–793.

H. Waldmann, "Manipulation of T–Cell responses with monoclonal antibodies", Am.Rev. Immunol. 1989, 7:407–44.

Mikhailov et al., "An evaluation of the possibility of Ebola fever specific prophylaxis in baboons", Voprosy Virusologil, No. 2, pp. 82–84, 1994.
GenBank Database printout, for Sanchez et al., Ebola virus nucleoprotine, polymerase complex protein (vp35), matrix protein (vp40), glycoprotein (gp), minor nucleoprotein (vp30), and membrane–associated structural protein (vp24)s, Oct. 14, 1997 (7 pages).
Grieder et al., "Specific restrictions in the progression of Venezuelan Equine Envephalitis virus–induced disease resulting from single amino acid changes in the glycoproteins", Virology 206, 994–1006 (1995).
Davis et al., "A viral vaccine vector that expresses foreign genes in lymph nodes and protects against mucosal challenge", J. Virology, Jun. 1996, vol. 70, pp. 3781–3787.
Xu et al., "Immunizatin for Ebola virus infection", Nature Medicine, vol. 4, No. 1, Jan. 1998, pp. 37–42.
Jahrling et al., "Evaluation of immune globulin and recombinant interferon–alpha2b for treatment of experimental Ebola virus infections", J. Infectious Diseases, 1999: 179(Suppl 1):S224–34.
Kudoyarova–Zubavichene et al., "Preparation and use of hyperimmune serum for prophylaxis and therapy of Ebola virus infections", J. Infectious Diseases, 1999:179(Suppl. 1):S218–23.
Maruyama et al., "Recombinant Human Monoclonal Antibodies to Ebola Virus", J. Infectious Diseases, 1999:179(Suppl. 1):S235–9.
Bray et al., "A mouse model for evaluation of prophylaxis and therapy of Ebola hemorrhagic fever", J. Infectious Diseases, 1998:178:651–61.
Sanchez et al., "The virion glycoproteins of Ebola viruses are encoded in two reading frames and are expressed through transcriptional editing", Proc.Natl.Acad.Sci. USA, vol. 93, pp. 3602–3607, Apr. 1996.
Pushko et la., "Venezuelan Equine Encephalitis Virus replicon vector: immunogenicity studies with Ebola NP and GP genes in guinea pigs", Vaccines 97, Molecular Approaches to the Control of Infectious Diseases, ed. Brown et al., Cold Spring Harbor Laboratory Press, 1997.

Hevey et al., "Antigenicity and vaccine potential of Marburg virus glycoprotein expressed by Baculovirus recombinants", Virology, 239, 206–216 (1997).

Pushko et al., "Replicon–helper systems from attenuated Venezuelan Equine Encephalitis virus: expression of heterologous genes in vitro and immunization against heterologous pathogens in vivo," Virology 239, 389–401 (1997).

Peters and LeDue, "An introduction to Ebola: The virus and the disease," J. Infectious Diseases, 1999:179(Suppl. 1):ix–xiv.

Sanchez et al., "Sequence analysis of the Ebola virus genome: organization, genetic elements, and comparison withthe genome of Marburg virus", Virus Research 29 (1993) 215–240.

Sullivan et al. "Accelerated vaccination for Ebola virus baemorrhagic fever in non–human primates", Letters to Nature, Nature, vol. 424, Aug. 7, 2003, pp. 681–684.

Sullivan et al., "Development of a preventive vaccine for Ebola virus infection in primates", Letters to Nature, Nature, 2000 (4 pages).

Sanchez et al., "Filoviridae: Marburg and Ebola Viruses", Chapter 40, Fields Virology, 4th Ed., 2001, Lippincott Williams and Wilkins, Philadelphia, editors: Knipe et al, pp. 1249–1304.

* cited by examiner

SEQUENCE LISTING

<160> NUMBER OF SEQ ID NOS: 40

<210> SEQ ID NO 1
<211> LENGTH: 2298
<212> TYPE: DNA
<213> ORGANISM: Ebola virus

<400> SEQUENCE: 1
atcgataagc tcggaattcg agctcgcccg gggatcctct agagtcgaca acaacacaat 60
gggcgttaca ggaatattgc agttacctcg tgatcgattc aagaggacat cattctttct 120
ttgggtaatt atccttttcc aaagaacatt ttccatccca cttggagtca tccacaatag 180
cacattacag gttagtgatg tcgacaaact agtttgtcgt gacaaactgt catccacaaa 240
tcaattgaga tcagttggac tgaatctcga agggaatgga gtggcaactg acgtgccatc 300
tgcaactaaa agatggggct tcaggtccgg tgtcccacca aaggtggtca attatgaagc 360
tggtgaatgg gctgaaaact gctacaatct tgaaatcaaa aaacctgacg ggagtgagtg 420
tctaccagca gcgccagacg ggattcgggg cttccccccgg tgccggtatg tgcacaaagt 480
atcaggaacg ggaccgtgtg ccggagactt tgccttccat aaagagggtg ctttcttcct 540
gtatgatcga cttgcttcca cagttatcta ccgaggaacg actttcgctg aaggtgtcgt 600
tgcatttctg atactgcccc aagctaagaa ggacttcttc agctcacacc ccttgagaga 660
gccggtcaat gcaacggagg acccgtctag tggctactat tctaccacaa ttagatatca 720
ggctaccggt tttggaacca atgagacaga gtacttgttc gaggttgaca atttgaccta 780
cgtccaactt gaatcaagat tcacaccaca gtttctgctc cagctgaatg agacaatata 840
tacaagtggg aaaaggagca ataccacggg aaaactaatt tggaaggtca accccgaaat 900
tgatacaaca atcggggagt gggccttctg ggaaactaaa aaaaacctca ctagaaaaat 960
tcgcagtgaa gagttgtctt tcacagttgt atcaaacgga gccaaaaaca tcagtggtca 1020
gagtccggcg cgaacttctt ccgacccagg gaccaacaca acaactgaag accacaaaat 1080
catggcttca gaaaattcct ctgcaatggt tcaagtgcac agtcaaggaa gggaagctgc 1140
agtgtcgcat ctaacaaccc ttgccacaat ctccacgagt ccccaatccc tcacaaccaa 1200
accaggtccg gacaacagca cccataatac acccgtgtat aaacttgaca tctctgaggc 1260
aactcaagtt gaacaacatc accgcagaac agacaacgac agcacagcct ccgacactcc 1320
ctctgccacg accgcagccg gacccccaaa agcagagaac accaacacga gcaagagcac 1380

-continued

```
tgacttcctg gaccccgcca ccacaacaag tccccaaaac cacagcgaga ccgctggcaa   1440
caacaacact catcaccaag ataccggaga agagagtgcc agcagcggga agctaggctt   1500
aattaccaat actattgctg gagtcgcagg actgatcaca ggcgggagaa gaactcgaag   1560
agaagcaatt gtcaatgctc aacccaaatg caaccctaat ttacattact ggactactca   1620
ggatgaaggt gctgcaatcg gactggcctg gataccatat ttcgggccag cagccgaggg   1680
aatttacata gaggggctaa tgcacaatca agatggttta atctgtgggt tgagacagct   1740
ggccaacgag acgactcaag ctcttcaact gttcctgaga gccacaactg agctacgcac   1800
cttttcaatc ctcaaccgta aggcaattga tttcttgctg cagcgatggg gcggcacatg   1860
ccacattctg ggaccggact gctgtatcga accacatgat tggaccaaga acataacaga   1920
caaaattgat cagattattc atgattttgt tgataaaacc cttccggacc agggggacaa   1980
tgacaattgg tggacaggat ggagacaatg gataccggca ggtattggag ttacaggcgt   2040
tgtaattgca gttatcgctt tattctgtat atgcaaattt gtcttttagt tttcttcag    2100
attgcttcat ggaaaagctc agcctcaaat caatgaaacc aggatttaat tatatggatt   2160
acttgaatct aagattactt gacaaatgat aatataatac actggagctt taaacatagc   2220
caatgtgatt ctaactcctt taaactcaca gttaatcata aacaaggttt gagtcgacct   2280
gcagccaagc ttatcgat                                                 2298
```

<210> SEQ ID NO 2
<211> LENGTH: 676
<212> TYPE: PRT
<213> ORGANISM: Ebola virus

<400> SEQUENCE: 2

```
Met Gly Val Thr Gly Ile Leu Gln Leu Pro Arg Asp Arg Phe Lys Arg
  1               5                  10                  15

Thr Ser Phe Phe Leu Trp Val Ile Ile Leu Phe Gln Arg Thr Phe Ser
             20                  25                  30

Ile Pro Leu Gly Val Ile His Asn Ser Thr Leu Gln Val Ser Asp Val
         35                  40                  45

Asp Lys Leu Val Cys Arg Asp Lys Leu Ser Ser Thr Asn Gln Leu Arg
     50                  55                  60

Ser Val Gly Leu Asn Leu Glu Gly Asn Gly Val Ala Thr Asp Val Pro
 65                  70                  75                  80

Ser Ala Thr Lys Arg Trp Gly Phe Arg Ser Gly Val Pro Pro Lys Val
                 85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205
```

-continued

```
Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620
```

-continued

Gln Ile Ile His Asp Phe Val Asp Lys Thr Leu Pro Asp Gln Gly Asp
625 630 635 640

Asn Asp Asn Trp Trp Thr Gly Trp Arg Gln Trp Ile Pro Ala Gly Ile
645 650 655

Gly Val Thr Gly Val Val Ile Ala Val Ile Ala Leu Phe Cys Ile Cys
660 665 670

Lys Phe Val Phe
675

<210> SEQ ID NO 3
<211> LENGTH: 105
<212> TYPE: PRT
<213> ORGANISM: Ebola virus

<400> SEQUENCE: 3

His Asn Thr Pro Val Tyr Lys Leu Asp Ile Ser Glu Ala Thr Gln Val
1 5 10 15

Glu Gln His His Arg Arg Thr Asp Asn Asp Ser Thr Ala Ser Asp Thr
20 25 30

Pro Ser Ala Thr Thr Ala Ala Gly Pro Pro Lys Ala Glu Asn Thr Asn
35 40 45

Thr Ser Lys Ser Thr Asp Phe Leu Asp Pro Ala Thr Thr Thr Ser Pro
50 55 60

Gln Asn His Ser Glu Thr Ala Gly Asn Asn Asn Thr His His Gln Asp
65 70 75 80

Thr Gly Glu Glu Ser Ala Ser Ser Gly Lys Leu Gly Leu Ile Thr Asn
85 90 95

Thr Ile Ala Gly Val Ala Gly Leu Ile
100 105

<210> SEQ ID NO 4
<211> LENGTH: 17
<212> TYPE: PRT
<213> ORGANISM: Ebola virus

<400> SEQUENCE: 4

Ala Thr Gln Val Glu Gln His His Arg Arg Thr Asp Asn Asp Ser Thr
1 5 10 15

Ala

<210> SEQ ID NO 5
<211> LENGTH: 9
<212> TYPE: PRT
<213> ORGANISM: Ebola virus

<400> SEQUENCE: 5

Glu Gln His His Arg Arg Thr Asp Asn
1 5

<210> SEQ ID NO 6
<211> LENGTH: 17
<212> TYPE: PRT
<213> ORGANISM: Ebola virus

<400> SEQUENCE: 6

His Asn Thr Pro Val Tyr Lys Leu Asp Ile Ser Glu Ala Thr Gln Val
1 5 10 15

Glu

-continued

<210> SEQ ID NO 7
<211> LENGTH: 9
<212> TYPE: PRT
<213> ORGANISM: Ebola virus

<400> SEQUENCE: 7

Val Tyr Lys Leu Asp Ile Ser Glu Ala
1 5

<210> SEQ ID NO 8
<211> LENGTH: 17
<212> TYPE: PRT
<213> ORGANISM: Ebola virus

<400> SEQUENCE: 8

Gly Lys Leu Gly Leu Ile Thr Asn Thr Ile Ala Gly Val Ala Gly Leu
1 5 10 15

Ile

<210> SEQ ID NO 9
<211> LENGTH: 9
<212> TYPE: PRT
<213> ORGANISM: Ebola virus

<400> SEQUENCE: 9

Leu Ile Thr Asn Thr Ile Ala Gly Val
1 5

<210> SEQ ID NO 10
<211> LENGTH: 295
<212> TYPE: PRT
<213> ORGANISM: Ebola virus

<400> SEQUENCE: 10

Met Gly Val Thr Gly Ile Leu Gln Leu Pro Arg Asp Arg Phe Lys Arg
1 5 10 15

Thr Ser Phe Phe Leu Trp Val Ile Ile Leu Phe Gln Arg Thr Phe Ser
20 25 30

Ile Pro Leu Gly Val Ile His Asn Ser Thr Leu Gln Val Ser Asp Val
35 40 45

Asp Leu Leu Val Cys Arg Asp Lys Leu Ser Ser Thr Asn Gln Leu Arg
50 55 60

Ser Val Gly Leu Asn Leu Glu Gly Asn Gly Val Ala Thr Asp Val Pro
65 70 75 80

Ser Ala Thr Lys Arg Trp Gly Phe Arg Ser Gly Val Pro Pro Lys Val
85 90 95

Val Asn Tyr Glu Ala Gly Glu Trp Ala Glu Asn Cys Tyr Asn Leu Glu
100 105 110

Ile Lys Lys Pro Asp Gly Ser Glu Cys Leu Pro Ala Ala Pro Asp Gly
115 120 125

Ile Arg Gly Phe Pro Arg Cys Arg Tyr Val His Lys Val Ser Gly Thr
130 135 140

Gly Pro Cys Ala Gly Asp Phe Ala Phe His Lys Glu Gly Ala Phe Phe
145 150 155 160

Leu Tyr Asp Arg Leu Ala Ser Thr Val Ile Tyr Arg Gly Thr Thr Phe
165 170 175

Ala Glu Gly Val Val Ala Phe Leu Ile Leu Pro Gln Ala Lys Lys Asp
180 185 190

Phe Phe Ser Ser His Pro Leu Arg Glu Pro Val Asn Ala Thr Glu Asp

-continued

```
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys
    290                 295
```

<210> SEQ ID NO 11
<211> LENGTH: 483
<212> TYPE: DNA
<213> ORGANISM: Artificial Sequence
<220> FEATURE:
<223> OTHER INFORMATION: Description of Artificial Sequence: Synthetic heavy chain of Mab EGP13C6-1-1 DNA sequence

<400> SEQUENCE: 11

```
actagtcgac atgggcagrc ttacwtcttc attcctgctg ctgattgtcc ctgcatatgt     60

cttgtyccaa cttactctaa aagagtctgg ccctgggata ttgaagccct cacagaccct    120

cagtctgact tgttctttat ctgggttttc actgagcact tctggtgtgg gtgtaggctg    180

gtttcgtcag ccttcaggga agggtctgga gtggctggca ctcatttggt gggatgatga    240

taaatactat aacccatccc tgaagagcca actctcaatc tccaaggatt tttccagaaa    300

ccaggtattc ctcaagatct ccaatgtgga cattgcagat actgccactt actactgtgc    360

tcgaagagac ccctttggtt acgacaatgc tatgggctat tggggtcaag gaacctcagt    420

caccgtctcc tcagccaaaa caacagcccc acccgtttat cccttggtcc ctggaagctt    480

ggg                                                                  483
```

<210> SEQ ID NO 12
<211> LENGTH: 157
<212> TYPE: PRT
<213> ORGANISM: Artificial Sequence
<220> FEATURE:
<223> OTHER INFORMATION: Description of Artificial Sequence: Synthetic heavy chain of Mab EGP13C6-1-1 amino acid sequence
<220> FEATURE:
<221> NAME/KEY: MOD_RES
<222> LOCATION: (19)
<223> OTHER INFORMATION: Variable amino acid

<400> SEQUENCE: 12

```
Met Gly Arg Leu Thr Ser Ser Phe Leu Leu Leu Ile Val Pro Ala Tyr
  1               5                  10                  15

Val Leu Xaa Gln Leu Thr Leu Lys Glu Ser Gly Pro Gly Ile Leu Lys
            20                  25                  30

Pro Ser Gln Thr Leu Ser Leu Thr Cys Ser Leu Ser Gly Phe Ser Leu
        35                  40                  45

Ser Thr Ser Gly Val Gly Val Gly Trp Phe Arg Gln Pro Ser Gly Lys
     50                  55                  60

Gly Leu Glu Trp Leu Ala Leu Ile Trp Trp Asp Asp Asp Lys Tyr Tyr
 65                  70                  75                  80
```

-continued

```
Asn Pro Ser Leu Lys Ser Gln Leu Ser Ile Ser Lys Asp Phe Ser Arg
                85                  90                  95

Asn Gln Val Phe Leu Lys Ile Ser Asn Val Asp Ile Ala Asp Thr Ala
            100                 105                 110

Thr Tyr Tyr Cys Ala Arg Arg Asp Pro Phe Gly Tyr Asp Asn Ala Met
        115                 120                 125

Gly Tyr Trp Gly Gln Gly Thr Ser Val Thr Val Ser Ser Ala Lys Thr
    130                 135                 140

Thr Ala Pro Pro Val Tyr Pro Leu Val Pro Gly Ser Leu
145                 150                 155
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic heavy chain of Mab EGP13C6-1-1 amino acid sequence

<400> SEQUENCE: 13

```
Thr Ser Gly Val Gly Val Gly
  1               5
```

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic heavy chain of Mab EGP13C6-1-1 amino acid sequence

<400> SEQUENCE: 14

```
Leu Ile Trp Trp Asp Asp Asp Lys Tyr Tyr Asn Pro Ser Leu Lys Ser
  1               5                  10                  15
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic heavy chain of Mab EGP13C6-1-1 amino acid sequence

<400> SEQUENCE: 15

```
Arg Asp Pro Phe Gly Tyr Asp Asn Ala Met Gly Tyr
  1               5                  10
```

<210> SEQ ID NO 16
<211> LENGTH: 446
<212> TYPE: DNA
<213> ORGANISM: Artificial Sequence
<220> FEATURE:
<223> OTHER INFORMATION: Description of Artificial Sequence: Synthetic light chain of Mab EGP13C6-1-1 DNA sequence

<400> SEQUENCE: 16

```
actagtcgac atgggcatca agatgaagtc acagacccag gcctttgtat tcgcgtttct     60

ctggttgtct ggtgttgatg gagacattgt gatgacccag tctcaaaaat tcatgtccac    120

atcagtagga gacagggtca gcctcacctg caaggccagt caaaatgtgg gtactgctgt    180

agcctggtat caacagaaac caggacaatc tcctaaacta ctgatttact cggcatccaa    240

tcggtacact ggagtccctg atcgcttcac aggcagtgga tctgggacag atttcactct    300

caccatcagc aatatgcagt ctgaagacct ggcagattat ttctgccagc aatatagcag    360
```

-continued

```
ctatccgctc acgttcggtg ctgggaccaa gctggagctg agacgggctg atgctgcacc    420

aactgtatcc atcttcccac catcca                                         446


<210> SEQ ID NO 17
<211> LENGTH: 145
<212> TYPE: PRT
<213> ORGANISM: Artificial Sequence
<220> FEATURE:
<223> OTHER INFORMATION: Description of Artificial Sequence: Synthetic
      light chain of Mab EGP13C6-1-1 amino acid sequence

<400> SEQUENCE: 17

Met Gly Ile Lys Met Lys Ser Gln Thr Gln Ala Phe Val Phe Ala Phe
  1               5                  10                  15

Leu Trp Leu Ser Gly Val Asp Gly Asp Ile Val Met Thr Gln Ser Gln
             20                  25                  30

Lys Phe Met Ser Thr Ser Val Gly Asp Arg Val Ser Leu Thr Cys Lys
         35                  40                  45

Ala Ser Gln Asn Val Gly Thr Ala Val Ala Trp Tyr Gln Gln Lys Pro
     50                  55                  60

Gly Gln Ser Pro Lys Leu Leu Ile Tyr Ser Ala Ser Asn Arg Tyr Thr
 65                  70                  75                  80

Gly Val Pro Asp Arg Phe Thr Gly Ser Gly Ser Gly Thr Asp Phe Thr
                 85                  90                  95

Leu Thr Ile Ser Asn Met Gln Ser Glu Asp Leu Ala Asp Tyr Phe Cys
            100                 105                 110

Gln Gln Tyr Ser Ser Tyr Pro Leu Thr Phe Gly Ala Gly Thr Lys Leu
        115                 120                 125

Glu Leu Arg Arg Ala Asp Ala Ala Pro Thr Val Ser Ile Phe Pro Pro
    130                 135                 140

Ser
145


<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      light chain of Mab EGP13C6-1-1 amino acid sequence

<400> SEQUENCE: 18

Lys Ala Ser Gln Asn Val Gly Thr Ala Val Ala
  1               5                  10


<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain of Mab EGP13C6-1-1 amino acid sequence

<400> SEQUENCE: 19

Ser Ala Ser Asn Arg Tyr Thr
  1               5


<210> SEQ ID NO 20
<211> LENGTH: 9
<212> TYPE: PRT
<213> ORGANISM: Artificial Sequence
```

-continued

<220> FEATURE:
<223> OTHER INFORMATION: Description of Artificial Sequence: Synthetic
light chain of Mab EGP13C6-1-1 amino acid sequence

<400> SEQUENCE: 20

```
Gln Gln Tyr Ser Ser Tyr Pro Leu Thr
  1               5
```

<210> SEQ ID NO 21
<211> LENGTH: 462
<212> TYPE: DNA
<213> ORGANISM: Artificial Sequence
<220> FEATURE:
<223> OTHER INFORMATION: Description of Artificial Sequence: Synthetic
heavy chain of Mab EGP6D8-1-2 DNA sequence

<400> SEQUENCE: 21

```
actagtcgac atggattttg ggctgatttt ttttattgtt gctcttttaa aaggggtcca     60

gtgtgatgtg aagcttctcg agtctggagg tggcctggtg cagcctggag gatccctgaa    120

actctcctgt gcagcctcag gattcgattt tagtagatac tggatgagtt gggtccggca    180

ggctccaggg aaagggctag aatggattgg agaaattaat ccagatagca gtacgataaa    240

ctatacgcca tctctaaagg ataaattcat catctccaga gacaacgcca aaaatacgct    300

gtacctgcaa atgagcaaag tgagatctga ggacacagcc ctttattact gtacaagaca    360

gggctacggc tacaattact ggggccaagg caccactctc atagtctcct cagccaaaac    420

aacagcccca cccgtctatc ccctggtccc tggaagcttg gg                       462
```

<210> SEQ ID NO 22
<211> LENGTH: 150
<212> TYPE: PRT
<213> ORGANISM: Artificial Sequence
<220> FEATURE:
<223> OTHER INFORMATION: Description of Artificial Sequence: Synthetic
heavy chain of Mab EGP6D8-1-2 amino acid sequence

<400> SEQUENCE: 22

```
Met Asp Phe Gly Leu Ile Phe Phe Ile Val Ala Leu Leu Lys Gly Val
  1               5                  10                  15

Gln Cys Asp Val Lys Leu Leu Glu Ser Gly Gly Gly Leu Val Gln Pro
             20                  25                  30

Gly Gly Ser Leu Lys Leu Ser Cys Ala Ala Ser Gly Phe Asp Phe Ser
         35                  40                  45

Arg Tyr Trp Met Ser Trp Val Arg Gln Ala Pro Gly Lys Gly Leu Glu
     50                  55                  60

Trp Ile Gly Glu Ile Asn Pro Asp Ser Ser Thr Ile Asn Tyr Thr Pro
 65                  70                  75                  80

Ser Leu Lys Asp Lys Phe Ile Ile Ser Arg Asp Asn Ala Lys Asn Thr
                 85                  90                  95

Leu Tyr Leu Gln Met Ser Lys Val Arg Ser Glu Asp Thr Ala Leu Tyr
            100                 105                 110

Tyr Cys Thr Arg Gln Gly Tyr Gly Tyr Asn Tyr Trp Gly Gln Gly Thr
        115                 120                 125

Thr Leu Ile Val Ser Ser Ala Lys Thr Thr Ala Pro Pro Val Tyr Pro
    130                 135                 140

Leu Val Pro Gly Ser Leu
145                 150
```

<210> SEQ ID NO 23

-continued

<211> LENGTH: 5
<212> TYPE: PRT
<213> ORGANISM: Artificial Sequence
<220> FEATURE:
<223> OTHER INFORMATION: Description of Artificial Sequence: Synthetic
heavy chain of Mab EGP6D8-1-2 amino acid sequence

<400> SEQUENCE: 23

Arg Tyr Trp Met Ser
1 5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
heavy chain of Mab EGP6D8-1-2 amino acid sequence

<400> SEQUENCE: 24

Glu Ile Asn Pro Asp Ser Ser Thr Ile Asn Tyr Thr Pro Ser Leu Lys
1 5 10 15

Asp

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
heavy chain of Mab EGP6D8-1-2 amino acid sequence

<400> SEQUENCE: 25

Gln Gly Tyr Gly Tyr Asn Tyr
1 5

<210> SEQ ID NO 26
<211> LENGTH: 453
<212> TYPE: DNA
<213> ORGANISM: Artificial Sequence
<220> FEATURE:
<223> OTHER INFORMATION: Description of Artificial Sequence: Synthetic
light chain of Mab EGP6D8-1-2 DNA sequence

<400> SEQUENCE: 26
gtcgacatga agttgcctgt taggctgttg gtgctgatgt tctggattcc tgcttccagc 60
agtgatgttt tgctgaccca aattccactc tccctgcctg tcagtcttgg agatcaagcg 120
tccatctctt gcagatctag tcagagtatt gttcatagta atggaaacac ctatttagaa 180
tggtacctgc agaaaccagg ccagtctcca aagctcctga tctacaaagc ttccaaccga 240
ttttctgggg tcccagacag gttcagtggc agtggatcag ggacagattt cacactcaag 300
atcaacagag tggaggctga ggatctggga gtttattact gccttcaagg ttcacatgtg 360
ccgtccacgt tcggaggggg gaccaagctg gaaataaaac gggctgatgc tgcaccaact 420
gtatccatct tcccaccatc cagtaagctt ggg 453

<210> SEQ ID NO 27
<211> LENGTH: 149
<212> TYPE: PRT
<213> ORGANISM: Artificial Sequence
<220> FEATURE:
<223> OTHER INFORMATION: Description of Artificial Sequence: Synthetic
light chain of Mab EGP6D8-1-2 amino acid sequence

<400> SEQUENCE: 27

-continued

```
Met Lys Leu Pro Val Arg Leu Leu Val Leu Met Phe Trp Ile Pro Ala
  1               5                  10                  15

Ser Ser Ser Asp Val Leu Leu Thr Gln Ile Pro Leu Ser Leu Pro Val
             20                  25                  30

Ser Leu Gly Asp Gln Ala Ser Ile Ser Cys Arg Ser Ser Gln Ser Ile
         35                  40                  45

Val His Ser Asn Gly Asn Thr Tyr Leu Glu Trp Tyr Leu Gln Lys Pro
     50                  55                  60

Gly Gln Ser Pro Lys Leu Leu Ile Tyr Lys Ala Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Asn Arg Val Glu Ala Glu Asp Leu Gly Val Tyr Tyr Cys
            100                 105                 110

Leu Gln Gly Ser His Val Pro Ser Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Lys Leu Gly
145
```

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic light chain of Mab EGP6D8-1-2 amino acid sequence

<400> SEQUENCE: 28

```
Arg Ser Ser Gln Ser Ile Val His Ser Asn Gly Asn Thr Tyr Leu Glu
  1               5                  10                  15
```

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic light chain of Mab EGP6D8-1-2 amino acid sequence

<400> SEQUENCE: 29

```
Lys Ala Ser Asn Arg Phe Ser
  1               5
```

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic light chain of Mab EGP6D8-1-2 amino acid sequence

<400> SEQUENCE: 30

```
Leu Gln Gly Ser His Val Pro Ser Thr
  1               5
```

<210> SEQ ID NO 31
<211> LENGTH: 484
<212> TYPE: DNA
<213> ORGANISM: Artificial Sequence
<220> FEATURE:

-continued

<223> OTHER INFORMATION: Description of Artificial Sequence: Synthetic
heavy chain of Mab EGP13F6-1-2 DNA sequence

<400> SEQUENCE: 31

```
gggaattcat ggagttgggg ctaagctgga ttttccttgt ccttactttg aaaggtgtga     60

agtgtgaagt gcaggtggtg gagtctgggg gaggcttagt gaagcctgga gggtccctga    120

aactctcctg tgcagcctct ggattcgctt tcagtagcta tgacatgtct tgggttcgcc    180

agactccgga gaagaggctg gagtgggtcg catacattag tcgtggtggt ggttacacct    240

actatccaga cactgtgaag ggccgattca ccatctccag agacaatgcc aagaacaccc    300

tgtacctgca aatgagcagt ctgaagtctg aggacacagc catgtattac tgttcaagac    360

atatatatta cgggagtagt cattactatg ctatggacta ctggggtcaa ggaacctcag    420

tcaccgtctc ctcagccaaa acaacagccc cacccgtcta tcccctggcc cctggaagct    480

tggg                                                                 484
```

<210> SEQ ID NO 32
<211> LENGTH: 158
<212> TYPE: PRT
<213> ORGANISM: Artificial Sequence
<220> FEATURE:
<223> OTHER INFORMATION: Description of Artificial Sequence: Synthetic
heavy chain of Mab EGP13F6-1-2 amino acid sequence

<400> SEQUENCE: 32

```
Met Glu Leu Gly Leu Ser Trp Ile Phe Leu Val Leu Thr Leu Lys Gly
  1               5                  10                  15

Val Lys Cys Glu Val Gln Val Val Glu Ser Gly Gly Gly Leu Val Lys
             20                  25                  30

Pro Gly Gly Ser Leu Lys Leu Ser Cys Ala Ala Ser Gly Phe Ala Phe
         35                  40                  45

Ser Ser Tyr Asp Met Ser Trp Val Arg Gln Thr Pro Glu Lys Arg Leu
     50                  55                  60

Glu Trp Val Ala Tyr Ile Ser Arg Gly Gly Gly Tyr Thr Tyr Tyr Pro
 65                  70                  75                  80

Asp Thr Val Lys Gly Arg Phe Thr Ile Ser Arg Asp Asn Ala Lys Asn
                 85                  90                  95

Thr Leu Tyr Leu Gln Met Ser Ser Leu Lys Ser Glu Asp Thr Ala Met
            100                 105                 110

Tyr Tyr Cys Ser Arg His Ile Tyr Tyr Gly Ser Ser His Tyr Tyr Ala
        115                 120                 125

Met Asp Tyr Trp Gly Gln Gly Thr Ser Val Thr Val Ser Ser Ala Lys
    130                 135                 140

Thr Thr Ala Pro Pro Val Tyr Pro Leu Ala Pro Gly Ser Leu
145                 150                 155
```

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
heavy chain of Mab EGP13F6-1-2 amino acid sequence

<400> SEQUENCE: 33

```
Ser Tyr Asp Met Ser
  1               5
```

-continued

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic heavy chain of Mab EGP13F6-1-2 amino acid sequence

<400> SEQUENCE: 34

```
Tyr Ile Ser Arg Gly Gly Gly Tyr Thr Tyr Tyr Pro Asp Thr Val Lys
  1               5                  10                  15

Gly
```

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic heavy chain of Mab EGP13F6-1-2 amino acid sequence

<400> SEQUENCE: 35

```
His Ile Tyr Tyr Gly Ser Ser His Tyr Tyr Ala Met Asp Tyr
  1               5                  10
```

<210> SEQ ID NO 36
<211> LENGTH: 847
<212> TYPE: DNA
<213> ORGANISM: Artificial Sequence
<220> FEATURE:
<223> OTHER INFORMATION: Description of Artificial Sequence: Synthetic light chain of Mab EGP13F6-1-2 DNA sequence

<400> SEQUENCE: 36

```
gggaattcat ggcctggatt ycwctyatct tctttgttct tcattgctca ggttctttct     60

cccaacttgt gctcactcag tcatcttcag cctctttctc cctgggagcc tcagcaaaac    120

tcacgtgcac cttgagtcgt cagcacagta cgtacaccat tgaatggtat cagcaacagc    180

cactcaagcc tcctaggtat gtgatggagc ttaagaaaga tggaagccac agcacaggtg    240

atgggattcc tgatcgcttc tctggatcca gctctggtgc tgatcgctac cttagcattt    300

ccaacatcca gcctgaagat gaagcaatat acatctgtgg tgtgggtgat acaattaagg    360

aacaatttgt gtatgttttc ggcggtggaa ccaaggtcac tgtcctaggt cagcccaagt    420

ccactcccac tctcaccgtg tttccacctt cctctgagga gctcaaggaa aacaaagcca    480

cactggtgtg tctgatttcc aacttttccc cgagtggtgt gacagtggcc tggaaggcaa    540

atggtacacc tatcacccag ggtgtggaca cttcaaatcc caccaaagag ggcaacaagt    600

tcatggccag cagcttccta catttgacat cggaccagtg gagatctcac aacagtttta    660

cctgtcaagt tacacatgaa ggggacactg tggagaagag tctgtctcct gcagaatgtc    720

tctaagaacc caggtttctc cttagcctgg gaaccctgca gcttttagag acccagggtg    780

gggtctcttc tttatattag ctatcttaac ccttcttccc accctccact gaggagctaa    840

gcttggg                                                              847
```

<210> SEQ ID NO 37
<211> LENGTH: 238
<212> TYPE: PRT
<213> ORGANISM: Artificial Sequence
<220> FEATURE:
<223> OTHER INFORMATION: Description of Artificial Sequence: Synthetic light chain of Mab EGP13F6-1-2 amino acid sequence
<220> FEATURE:

-continued

<221> NAME/KEY: MOD_RES
<222> LOCATION: (5)
<223> OTHER INFORMATION: Variable amino acid

<400> SEQUENCE: 37

```
Met Ala Trp Ile Xaa Leu Ile Phe Phe Val Leu His Cys Ser Gly Ser
  1               5                  10                  15

Phe Ser Gln Leu Val Leu Thr Gln Ser Ser Ser Ala Ser Phe Ser Leu
             20                  25                  30

Gly Ala Ser Ala Lys Leu Thr Cys Thr Leu Ser Arg Gln His Ser Thr
         35                  40                  45

Tyr Thr Ile Glu Trp Tyr Gln Gln Gln Pro Leu Lys Pro Pro Arg Tyr
     50                  55                  60

Val Met Glu Leu Lys Lys Asp Gly Ser His Ser Thr Gly Asp Gly Ile
 65                  70                  75                  80

Pro Asp Arg Phe Ser Gly Ser Ser Ser Gly Ala Asp Arg Tyr Leu Ser
                 85                  90                  95

Ile Ser Asn Ile Gln Pro Glu Asp Glu Ala Ile Tyr Ile Cys Gly Val
            100                 105                 110

Gly Asp Thr Ile Lys Glu Gln Phe Val Tyr Val Phe Gly Gly Gly Thr
        115                 120                 125

Lys Val Thr Val Leu Gly Gln Pro Lys Ser Thr Pro Thr Leu Thr Val
    130                 135                 140

Phe Pro Pro Ser Ser Glu Glu Leu Lys Glu Asn Lys Ala Thr Leu Val
145                 150                 155                 160

Cys Leu Ile Ser Asn Phe Ser Pro Ser Gly Val Thr Val Ala Trp Lys
                165                 170                 175

Ala Asn Gly Thr Pro Ile Thr Gln Gly Val Asp Thr Ser Asn Pro Thr
            180                 185                 190

Lys Glu Gly Asn Lys Phe Met Ala Ser Ser Phe Leu His Leu Thr Ser
        195                 200                 205

Asp Gln Trp Arg Ser His Asn Ser Phe Thr Cys Gln Val Thr His Glu
    210                 215                 220

Gly Asp Thr Val Glu Lys Ser Leu Ser Pro Ala Glu Cys Leu
225                 230                 235
```

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic light chain of Mab EGP13F6-1-2 amino acid sequence

<400> SEQUENCE: 38

```
Thr Leu Ser Arg Gln His Ser Thr Tyr Thr Ile Glu
  1               5                  10
```

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic light chain of Mab EGP13F6-1-2 amino acid sequence

<400> SEQUENCE: 39

```
Leu Lys Lys Asp Gly Ser His Ser Thr Gly Asp
  1               5                  10
```

-continued

```
<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      light chain of Mab EGP13F6-1-2 amino acid sequence

<400> SEQUENCE: 40

Gly Val Gly Asp Thr Ile Lys Glu Gln Phe Val Tyr Val
  1               5                  10
```

MONOCLONAL ANTIBODIES AND COMPLEMENTARITY-DETERMINING REGIONS BINDING TO EBOLA GLYCOPROTEIN

BACKGROUND OF THE INVENTION

Ebola viruses cause acute, lethal hemorrhagic fevers for which no human-use vaccines or treatments currently exist. Knowledge about the immune mechanisms mediating protection is limited. The membrane-anchored glycoprotein (GP) is the only viral protein known to be on the surfaces of virions and infected cells, and is presumed to be responsible for receptor binding and fusion of the virus with host cells. As a result, Ebola GP may be an important target of protective antibodies. However, the contribution of antibodies to Ebola GP in disease resistance has been controversial. Negligible serum titers of neutralizing antibodies in convalescent patients, together with inconsistent results in achieving protection through experimental transfers of immune sera to animals (C. J. Peters and J. W. LeDuc, J. Infect. Dis. 179 (Suppl. 1), ix, 1999; V. V. Mikhailov et al., Vopr. Virusol. 39, 82, 1994) have led to suggestions that antibodies to Ebola GP cannot confer protection to Ebola virus (L. Xu et al., Nature Med. 4, 37, 1998).

The role of anti-GP antibodies in protection is further confounded by the observation that Ebola GP occurs in several forms. The transmembrane glycoprotein of Ebola viruses is unusual in that it is encoded in two open reading frames. Expression of GP occurs when the 2 reading frames are connected by transcriptional or translational editing (Sanchez et al., Proc. Natl. Acad. Sci. USA 93, 3602–3607, 1996; Volchkov et al., Virology 214, 421–430, 1995). The unedited GP mRNA produces a non-structural secreted glycoprotein (sGP) that is synthesized in large amounts early during the course of infection (Volchkov et al., 1995, supra; Sanchez et al., 1996, supra; Sanchez et al., J. Infect. Dis. 179 (suppl. 1, S164, 1999). Following editing, the virion-associated transmembrane glycoprotein is proteolytically processed into 2 disulfide-linked products (Sanchez et al., J. Virol. 72, 6442–6447, 1998). The amino-terminal product is referred to as GP1 (140 kDa) and the carboxy-terminal cleavage product is referred to as GP2 (26 kDa). GP1 and membrane-bound GP, covalently associate to form a monomer of the GP spike found on the surfaces of virions (V. E. Volchkov et al., Proc. Natl. Acad. Sci. U.S.A. 95, 5762, 1998; A. Sanchez et al., J. Virol. 72, 6442, 1998). GP1 is also released from infected cells in a soluble form (V. E. Volchkov. et al., Virology 245, 110, 1998). sGP and GP1 are identical in their first 295 N-terminal amino acids, whereas the remaining 69 C-terminal amino acids of sGP and 206 amino acids of GP 1 are encoded by different reading frames. It has been suggested that secreted GP 1 or sGP may effectively bind antibodies that might otherwise be protective (Sanchez et al., 1996, supra; Volchkov et al. 1998, supra).

Ebola virus GP is a type I transmembrane glycoprotein. Comparisons of the predicted amino acid sequences for the GPs of the different Ebola virus strains show conservation of amino acids in the amino-terminal and carboxy-terminal regions with a highly variable region in the middle of the protein (Feldmann et al., Virus Res. 24: 1–19, 1992). The GP of Ebola viruses are highly glycosylated and contain both N-linked and O-linked carbohydrates that contribute up to 50% of the molecular weight of the protein. Most of the glycosylation sites are found in the central variable region of GP.

Other studies have also demonstrated limited efficacy of passively transferred polyclonal antibodies in protection against Ebola challenge (Mikhailov et al, 1994, Voprosi Virusologii, 39, 82–84; Jahrling et al., 1996, Arch Virol, 11S, 135–140; Jahrling et al., 1999, J Infect Dis, 179 (Suppl 1), S224–234; Kudoyarova-Zubavichene et al., 1999, J Infect Dis, 179(Suppl 1), S218–223). However, it is difficult to determine the effective therapeutic dose of antibodies in different preparations of polyclonal antibodies. Efforts to identify the role of antibodies in protection led to the isolation of monoclonal antibodies from mice vaccinated with Ebola GP (for instance, co-pending patent application Ser. No. 09/650,086; and Wilson et al. Science 287, 1664, 2000), and from convalescent people (Maruyama et al. J. Infect. Dis. 179 (suppl 1), S235, 1999; Maruyama et al. J. Virol. 73, 6024, 1999; Parren et al. J. Virol 76, 6408, 2002). These were tested in rodents and protected against lethal infection (Wilson et al. Science 287, 1664,2000; Parren et al. J. Virol 76, 6408, 2002).

SUMMARY OF THE INVENTION

This application describes protective GP-specific MAbs. The antibodies are classified into five groups based on competitive binding assays. Individual MAbs in these five groups were protective against Ebola challenge when administered prophylactically or therapeutically. (By "prophylactic", it is meant administered before challenge, and by "therapeutic", it is meant administered after challenge.) Three of the epitopes bound by protective MAbs are linear sequences on GP1 whereas the other two are conformational epitopes shared between GP1 and sGP. Ten out of 14 MAbs identified in these five competition groups protected BALB/c mice from a lethal challenge with mouse-adapted Ebola Zaire virus when 100 ug of purified MAb was administered 24 hours before challenge (please see Table 3 in Examples below). Similar results were observed in a second mouse strain (C57BL/6). Protection from Ebola challenge decreased when the MAb dose was lowered to 50 or 25 ug (Please see Table 3 and Table 5 in Examples below). For the most effective MAbs, the amount required for protection was within an achievable human therapeutic dose of 3–5 mg/kg. Some of the MAbs were effective even when administered up to 2 days after challenge (please see Table 3 in Examples below), after significant viral replication had occurred (M. Bray et al., J. Infect. Dis. 178, 651, 1998). None of the MAbs were protective when 100 ug was administered 3 days after challenge, when there are high viral titers (Bray et al., 1998, supra) and possibly irreversible damage of cells and organs. The ability of the MAbs to inhibit plaque formation by Ebola virus, a standard assay of virus neutralization, did not always predict their protective efficacy. None of the protective MAbs inhibited plaque formation in the absence of complement (please see Table 6 in the Examples below).

One embodiment of this invention relates to monoclonal antibodies that protect against Ebola virus and bind to epitopes on the Ebola virus GP. Such antibodies are, for instance, produced by any one of the cell lines deposited under the Budapest Treaty at American Type Culture Collection, Manassas, Va. on Jul. 20, 1999, EGP 13F6-1-2, assigned accession no. PTA-373, EGP 6D3-1-1 assigned accession no. PTA-374, EGP 13-C6-1-1 assigned accession no. PTA-375, EGP 6D8-1-2 assigned accession no. PTA-376 and EGP 12B5-1-1 deposited on Jul. 29, 1999 and assigned accession no. PTA-436 (Table 1).

TABLE 1

| Monoclonal | Hybridoma | ATCC accession no. |
|---|---|---|
| MAb 6D8 | EGP 6D8-1-2 | PTA-376 |
| MAb 13F6 | EGP 13F6-1-2 | PTA-373 |
| MAb 12B5 | EGP 12B5-1-1 | PTA-436 |
| MAb 13C6 | EGP 13-C6-1-1 | PTA-375 |
| MAb 6D3. | EGP 6D3-1-1 | PTA-374 |

Another embodiment relates to the sequences of these monoclonal antibodies, in particular, the sequences to MAb EGP 6D8-1-2, MAb EGP 13F6-1-2, and Mab EGP 13-C6-1-1.

A further embodiment relates to the complementarity-determining regions of these three monoclonal antibodies (MAb EGP 6D8-1-2, MAb EGP 13F6-1-2, and Mab EGP 13-C6-1-1) which are involved with the binding of the monoclonal antibodies to Ebola virus.

Another embodiment of the invention relates to antibodies that are functionally equivalent to the antibodies listed above. These functionally equivalent antibodies substantially share at least one major functional property with an antibody listed above and herein described comprising: binding specificity to Ebola GP, protection against Ebola challenge when administered prophylactically or therapeutically, competition for same binding site on Ebola GP, and/or use of the same combination of complementarity determining regions. The antibodies can be of any class such as IgG, IgM, or IgA or any subclass such as IgG1, IgG2a, and other subclasses known in the art. Further, the antibodies can be produced by any method, such as phage display, or produced in any organism or cell line, including bacteria, insect, mammal or other type of cell or cell line which produces antibodies with desired characteristics, such as humanized antibodies. The antibodies can also be formed by combining a Fab portion and a Fc region from different species, or by keeping the complementarity-determining regions and modifying the framework regions to that of another species (such a human, which is described in more detail below).

The monoclonal antibodies of the present invention described below recognize epitopes on Ebola GP (SEQ ID NO: 1 and 2 describe the DNA and amino acid sequence, respectively, of Ebola GP used as an immunogen). Three epitopes are within the sequence extending from 389 to 493 and defined as:

```
HNTPVYKLDISEATQVEQHHRRTDNDSTASDTPSATTAAGPPKAENTNTSKSTDF  (SEQ ID NO:3)

LDPATTTSPQNHSETAGNNNTHHQDTGEESASSGKLGLITNTIAGVAGLI.
```

More specifically, the cell line EGP 13F6-1-2 produces a monoclonal antibody 13F6 which recognizes and binds to an amino acid sequence of GP corresponding to a region extending from 401 to 417 (SEQ ID NO:4), recognizing an epitope within this region corresponding to Glu-Gln-His-His-Arg-Arg-Thr-Asp-Asn (SEQ ID NO:5). The cell line EGP 6D8-1-2 produces a monoclonal antibody 6D8 which recognizes and binds to an amino acid sequence of GP corresponding to a region extending from 389 to 405 (SEQ ID NO:6), recognizing an epitope within this region corresponding to Val-Tyr-Lys-Leu-Asp-Ile-Ser-Glu-Ala (SEQ ID NO:7). The cell line EGP 12B5-1-1 produces a monoclonal antibody 12B5 which recognizes and binds to an amino acid sequence of GP corresponding to a region extending from 477 to 493 (SEQ ID NO:8), recognizing an epitope within this region corresponding to Leu-Ile-Thr-Asn-Thr-Ile-Ala-Gly-Val (SEQ ID NO:9). The antibodies produced by cell lines EGP 13C6-1-1, 13C6, and EGP 6D3-1-1, 6D3, recognize conformational epitopes in GP sequence that may comprise discontinuous Ebola virus amino acids that are conserved between Zaire and Ivory Coast viruses and found in the 295 amino terminus of the protein (SEQ ID NO:10).

A further embodiment of the present invention provides for mixtures of the above-described antibodies, as well as to methods of using individual antibodies, or mixtures thereof for the prevention and/or therapeutic treatment of Ebola infections in vitro and in vivo, and/or for improved detection of Ebola infections.

Another embodiment relates to the treatment or prevention of Ebola virus infection by administering a therapeutically or prophylactically effective amount of one antibody of the present invention or a mixture of antibodies of the present invention to a subject in need of such treatment.

A further embodiment provides passive vaccines for treating or preventing Ebola virus infections comprising a therapeutically or prophylactically effective amount of the antibodies of the present invention which protect against Ebola virus, in combination with a pharmaceutically acceptable carrier or excipient.

Yet another embodiment provides methods for diagnosis of Ebola virus infection by assaying for the presence of Ebola in a sample using the antibodies of the present invention.

Still another embodiment provides novel immunoprobes and test kits for detection of Ebola virus infection comprising antibodies according to the present invention. For immunoprobes, the antibodies are directly or indirectly attached to a suitable reporter molecule, e.g., and enzyme or a radionuclide. The test kit includes a container holding one or more antibodies according to the present invention and instructions for using the antibodies for the purpose of binding to Ebola virus to form an immunological complex and detecting the formation of the immunological complex such that presence or absence of the immunological complex correlates with presence or absence of Ebola virus.

In another embodiment, there are provided anti-idiotypic antibodies raised against one of the present monoclonal antibodies for use as a vaccine to elicit an active anti-GP response.

In a further embodiment, there are provided antigenic epitopes as a component of a Ebola virus vaccine. The epitopes described above comprising SEQ ID NO:3–10, or conservative changes thereof which are still recognized by the antibodies, are useful for actively immunizing a host to elicit production of protective antibodies against Ebola.

BRIEF DESCRIPTION OF THE DRAWINGS

These and other features, aspects, and advantages of the present invention will become better understood with reference to the following description and appended claims, and accompanying drawings where:

DETAILED DESCRIPTION

Figure 1:
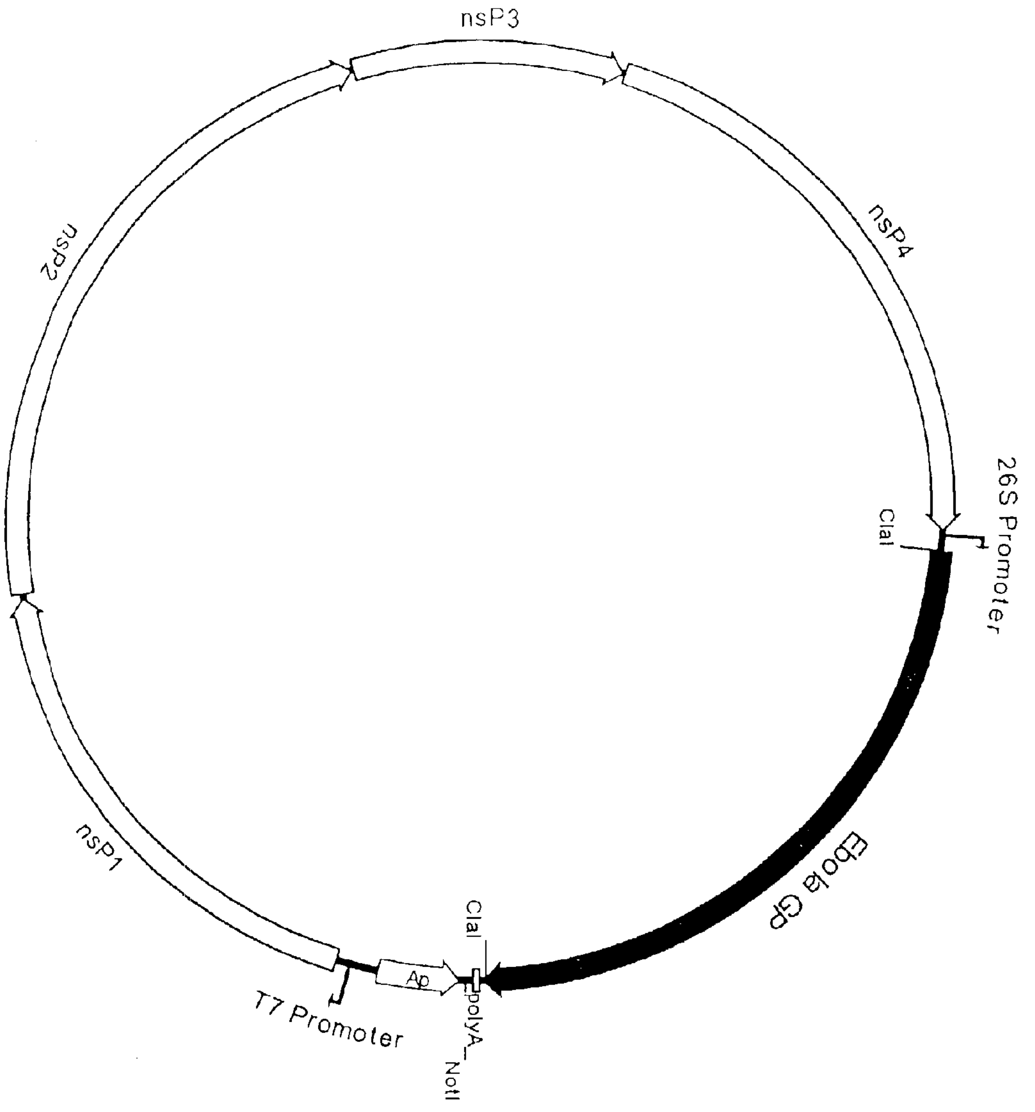
FIG. 1 illustrates the replicon VRepEboGP used make replicon particles EboGP-VRP. The particles were used to vaccinate mice for production of antibodies to Ebola GP.

In the description that follows, a number of terms used in recombinant DNA, virology and immunology are extensively utilized. In order to provide a clearer and consistent understanding of the specification and claims, including the scope to be given such terms, the following definitions are provided. "Ebola viruses", members of the family Filoviridae, are associated with outbreaks of highly lethal hemorrhagic fever in humans and nonhuman primates. Human pathogens include Ebola Zaire, Ebola Sudan, and Ebola Ivory Coast. Ebola Reston is a monkey pathogen and is not considered a human pathogen. The natural reservoir of the virus is unknown and there are currently no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection. Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al. (1992) Virus Res. 24, 1–19; Sanchez et al.,(1993) Virus Res. 29, 215–240; reviewed in Peters et al. (1996) In Fields Viroloqy, Third ed. pp. 1161–1176. Fields, B. N., Knipe, D. M., Howley, P. M., et al. eds. Lippincott-Raven Publishers, Philadelphia). The glycoprotein of Ebola virus is unusual in that it is encoded in two open reading frames. Transcriptional editing is needed to express the transmembrane form that is incorporated into the virion (Sanchez et al. (1996) Proc. Natl. Acad. Sci. USA 93, 3602–3607; Volchkov et al, (1995) Virology 214, 421–430). The unedited form produces a nonstructural secreted glycoprotein (sGP) that is synthesized in large amounts early during the course of infection. Little is known about the biological functions of these proteins and it is not known which antigens significantly contribute to protection and should therefore be used to induce an immune response.

The term "antibody" is art-recognized terminology and is intended to include molecules or active fragments of molecules that bind to known antigens. Examples of active fragments of molecules that bind to known antigens include Fab and F(ab')2 fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011–1019 (1982). The term "antibody" also includes bispecific and chimeric antibodies.

The language "monoclonal antibody" is art-recognized terminology. It is generally understood by those of skill in the art to refer to the antibody produced by one clone of B lymphocytes. The monoclonal antibodies of the present invention can be prepared using classical cloning and cell fusion techniques. The immunogen (antigen) of interest, Ebola GP protein, is typically administered (e.g. intraperitoneal injection) to wild type or inbred mice (e.g. BALB/c) or transgenic mice which produce desired antibodies, rats, rabbits or other animal species which can produce native or human antibodies. The immunogen can be administered alone, or mixed with adjuvant, or expressed from a vector (VEE replicon vector, vaccinia), or as DNA, or as a fusion protein to induce an immune response. Fusion proteins comprise the peptide against which an immune response is desired coupled to carrier proteins, such as b-galactosidase, glutathione S-transferase, keyhole limpet hemocyanin (KLH), and bovine serum albumin, to name a few. In these cases, the peptides serve as haptens with the carrier proteins. After the animal is boosted, for example, two or more times, the spleen can be removed and splenocytes can be extracted and fused with myeloma cells using the well-known processes of Kohler and Milstein (Nature 256: 495–497 (1975)) and Harlow and Lane (Antibodies: A Laboratory Manual (Cold Spring Harbor Laboratory, New York 1988)). The resulting hybrid cells can then be cloned in the conventional manner, e.g. using limiting dilution, and the resulting clones, which produce the desired monoclonal antibodies, cultured.

Monoclonal antibodies raised against Ebola GP as described in the Examples are listed in Table 1 above.

The monoclonal antibodies of this invention contain at least one "complementarity-determining region" (CDR). By "complementarity-determining region", it is meant the hypervariable regions in the heavy and light chains of an antibody molecule that form the 3-dimensional cavity by which the antibody binds to an epitope on the antigen.

The term "epitope" is art-recognized. It is generally understood by those of skill in the art to refer to the region of an antigen, such as Ebola virus GP, that interacts with an antibody. An epitope of a peptide or protein antigen can be formed by contiguous or noncontinguous amino acid sequences of the antigen. Ebola GP, like many large proteins, contains many epitopes. Examples of Ebola GP epitopes recognized by antibodies of the present invention include the region extending from 389 to 493 and defined as:

```
HNTPVYKLDISEATQVEQHHRRTDNDSTASDTPSATTAAGPPKAENTNTSKSTDF (SEQ ID NO:3)

LDPATTTSPQNIISETAGNNNTHHQDTGEESASSGKLGLINTIAGVAGLI.
```

Continuous epitopes were found within 1) the amino acid sequence of GP corresponding to a region extending from 401 to 417 (SEQ ID NO:4), for example corresponding to Glu-Gln-His-His-Arg-Arg-Thr-Asp-Asn (SEQ ID NO:5), 2) the amino acid sequence of GP corresponding to a region extending from 389 to 405 (SEQ ID NO:6), for example corresponding to Val-Tyr-Lys-Leu-Asp-Ile-Ser-Glu-Ala (SEQ ID NO:7), and 3) the amino acid sequence of GP corresponding to a region extending from 477 to 493 (SEQ ID NO:8), for example Leu-Ile-Thr-Asn-Thr-Ile-Ala-Gly- Val (SEQ ID NO:9). The epitopes or peptides recognized by the antibodies of the present invention and conservative substitutions of these peptides which are still recognized by the antibody are an embodiment of the present invention. These peptides offer a convenient method for eluting GP bound to MAb 6D8, 13F6, or 12B5 on immunoaffinity columns. For example, when an antibody which recognizes the epitope for MAb 6D8, 13F6 or 12B5 is used in an immunoaffinity column to purify Ebola GP, the peptide recognized by the antibody can be added to the immunoaffinity column to elute the Ebola GP. Further truncation of these epitopes may be possible, as would be understood by someone having ordinary skill in this art having this disclosure in hand.

Epitope mapping studies described in this application defined five competition groups of MAbs. Antibodies which compete with the monoclonal antibodies of the present invention for binding to GP are considered to recognize the epitopes of the antibodies and are considered equivalent to the antibodies of the present invention. The MAbs 13C6 and 6D3 recognize conformational epitopes comprising discontinuous Ebola virus amino acids. Antibodies which compete with MAbs 13C6 and 6D3 for binding to Ebola GP are considered to recognize discontinuous epitopes and are considered equivalent to the antibodies of the present invention. Assays for determining whether or not an antibody competes with an antibody of the present invention are known to a person with ordinary skill in the art and are described below. Table 2 below defines functional criteria of each of the monoclonal antibodies identified in the Examples below.

binds, (iii) narrowing the region containing sites further by reacting the monoclonal with smaller overlapping fragments encompassing the region identified in (ii), and (iv) choosing peptides to which the antibody binds as possible antigenic epitopes. The peptides can then be assayed for their ability to protect an animal from disease, or to reduce the severity of disease. Peptides defining antigenic protective epitopes can be used in a vaccine as described below and in the Examples.

The epitopes or peptides on Ebola GP to which the monoclonal antibodies bind can constitute all or part of an active vaccine. An active vaccine or therapeutic candidate might comprise these peptide sequences and others. These may be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective immune responses.

Antibody molecules produced in vivo comprise two identical heavy chains that are covalently bound and two identical light chains, each of which is covalently bound to a heavy chain. Heavy and light chains each have one variable region and three constant regions. Within the variable regions of light and heavy chains are hypervariable sequences called complementarity-determining regions flanked by framework regions. The binding specificity of an antibody is conferred by its combination of complementarity-determining regions. There are three complementarity-determining regions on the light chain and three on the heavy chain of an antibody molecule. Together,

TABLE 2

Epitopes Bound by Ebola GP MAbs.

| Competition Group | Ebola Viruses with Epitope* | Ebola GPs with Epitope[1] | Epitope Sequence on Ebola GP‡ | Amino Acids§ |
|---|---|---|---|---|
| 1 | Z | GP1 | ATQV**EQHHRRTDN**DSTA | 401–417 |
| 2 | Z | GP1 | HNTP**VYKLDISEA**TQVE | 389–405 |
| 3 | Z | GP1 | GKLG**LITNTTAGV**AGLI | 477–493 |
| 4 | Z, IC, S | GP1, sGP | discontinuous | 1–295 |
| 5 | Z, IC | GP1, sGP | discontinuous | 1–295 |

Figure 2:
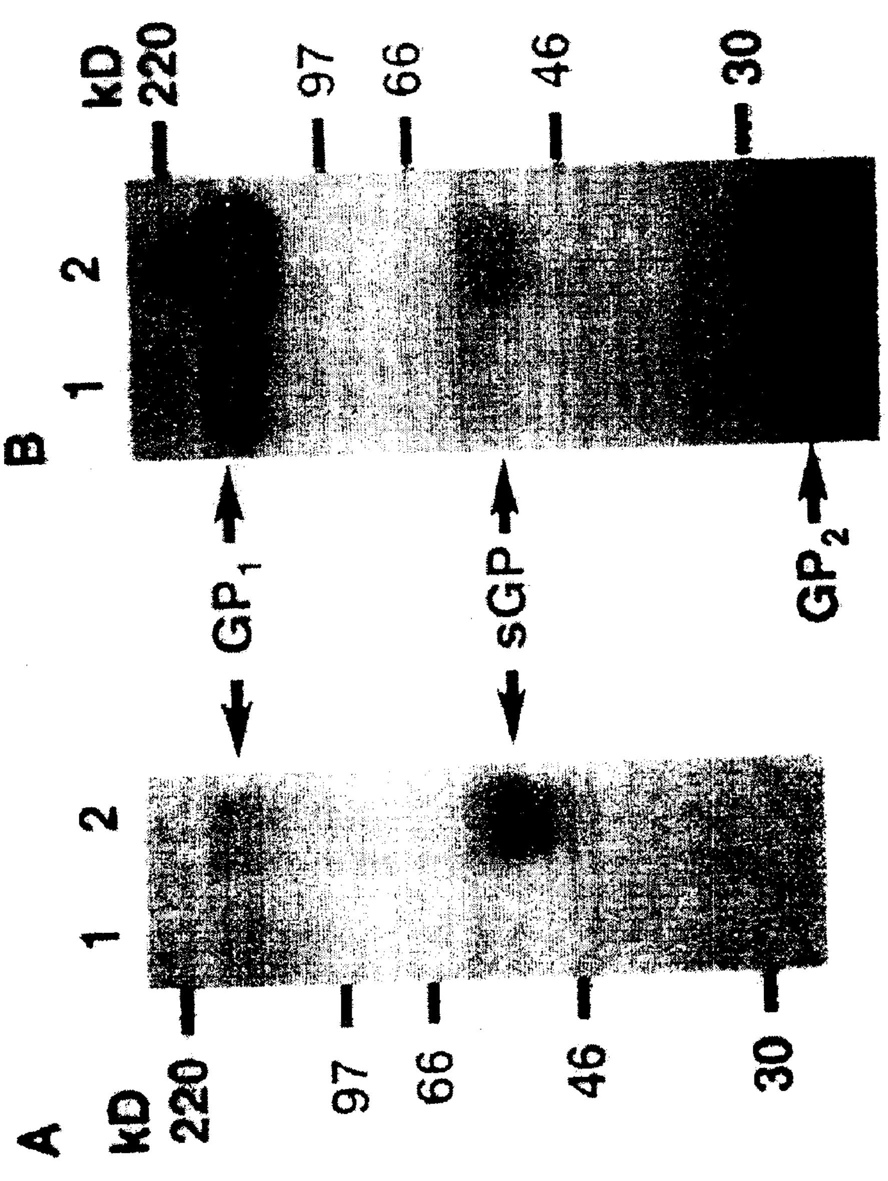
FIGS. 2A and 2B Immunoprecipitation of 35S-labeled Ebola GPs from supernatants of Vero cells infected with (A) EboGP-VRPs or (B) Ebola Zaire 1995 virus, with either the MAb 13F6 (Lane 1) or the MAb 13C6 (Lane 2). Both preparations contained secreted GP1 and sGP. Disulfide-linked GP1 and GP2 comprise the spikes on the virions that are also present in the Ebola-infected preparation (B). The immunoprecipitation of GPs with 13F6 was identical to that observed with MAbs 6D8 and 12B5. MAb 6D3 had reactivities identical to MAb 13C6. GP proteins were resolved under reducing conditions on an 11% SDS polyacrylamide gel.

*Reactivities of MAbs with Ebola Zaire (Z, isolates from 1976 and 1995), Sudan (S), and Ivory Coast (IC) viruses in ELISA.
[1]Determined by western blot reactivity with Ebola Zaire 1995 virions or by immunoprecipitation (FIG. 2).
‡MAbs bound two consecutive peptide sequences immobilized on SPOTS membranes. Each peptide was 13 amino acids long and had a 9 amino acid overlap with the preceding and subsequent peptides. Sequences in bold indicate the 9 amino acid overlapping consensus sequence found on both peptides bound by the MAbs. Peptides containing the entire amino acid sequence shown also competed the binding of MAbs to Ebola virions in ELISA.
§Amino acid numbers based on the GP sequence from Genbank (accession number U23187, A. Sanchez, S. G. et al. (1996) Proc. Natl. Acad. Sci., USA 93, 3602).

By further mapping of the binding site of the monoclonal antibodies described in this disclosure other peptides useful as a vaccine or a therapeutic can be determined using known methodologies. Therefore, in another aspect, this invention relates to a method for identifying protective antigenic epitopes, which method comprises the steps of (i) reacting a monoclonal antibody described herein to different overlapping fragments encompassing the complete antigen, (ii) identifying a fragment to which the protective antibody these form the 3-dimensional cavity that will bind (hold) an epitope on an antigen. Although these regions are hypervariable, a particular complementarity-determining region on one antibody may also be found on antibodies with different specificities, as it is the total combination of complementarity-determining regions that is important. Generally, binding specificity is determined by the complementarity-determining regions on both chains, although it has been suggested that the complementarity-determining regions on the heavy chain do not contribute to specificity when the light chain is produced by a gene called lambda x. Identification of the complementarity-determining regions is useful for changing the "speciation" of an antibody, for example changing a mouse antibody to a humanized form suitable for human use, because one would want to preserve the complementarity-determining regions so as not to eliminate the binding specificity. Using the numbering system of Kabat et al, (NIH Publication No. 91-3242, 1991) in which the signal sequences of the heavy and light chains are indicated with negative numbers, the complementarity-determining regions of the light chain are between amino acids 24–34 (CDR1), 50–56 (CDR2) and 89–97 (95 a–f, CDR3). The complementarity-determining regions of the heavy chain are between amino acids 31–35 (35 a–b, CDR1), 50–65 (52 a–c, CDR2), and 95–102 (100 a–k, CDR3). Insertions of extra amino acids into the complementarity-determining regions can be observed and their locations are represented above in parentheses, e.g 95 a–f. Deletions are also observed, for example in CDR3 of some types of heavy chains.

Throughout this description we refer to the CDRs in terms of both the amino acid sequence and the location within the light or heavy chain. As someone having ordinary skill in this art would understand, the "location" of the CDRs is conserved between species, but through the use the well known Kabat system—an arbitrary numbering system that aligns sequences. Therefore, according to the Kabat system, the first invariant amino acid of a given type of light chain might be used to define the CDR beginning at, for example, "position 24" even if there are not 23 preceding amino acids. Therefore, for the purposes of the description of this invention we are defining CDRs as according to the Kabat system which is accepted in the art. The Kabat system aligns the Mab sequences of different species, for example mouse and human, such that all species have CDRs aligned at the same numbered "positions". Alignment of the sequences occurs through the identification of invariant residues in either the CDR or the framework regions adjacent to the CDR. There are different forms of light and heavy chain variable regions that differ in the use and location of the invariant residues, but Kabat et al. identify these. Using the nomenclature in the 1991 edition of Kabat et al, Mab EGP 6D8-1–2 uses a heavy chain variable region of the IIID type, and a kappa light chain type II. Mab EGP 13C6-1-1 uses a heavy chain variable region of the miscellaneous type, and a kappa light chain type V. Mab EGP 13F6-1-2 uses a heavy chain variable region of the IIID type, and a lambda x light chain.

The DNA sequence of the variable regions of the heavy chain of Mab EGP13C6-1-1 is represented in SEQ ID NO:11, and the amino acid sequence is represented in SEQ ID NO:12. For the heavy chain, the CDRs were identified as located at the following amino acid positions:

31–35b (where, as noted above, "b" signifies the insertion of an extra amino acid) having the amino acid sequence TSGVGVG with the last two amino acids representing insertions at 35a and 35b (SEQ ID NO:13), 50–65: having the amino acid sequence LIWWD-DDKYYNPSLKS (SEQ ID NO:14), and 95–102 (includes residues at 100c,h,j,k, where, as noted above, "c,h,j,k" signifies the insertion of extra amino acids): having the amino acid sequence RDPFGYDNAMGY where DNAM are 100 c,h,j,k, respectively (SEQ ID NO:15).

It is believed that all three of these CDRs are necessary for effective binding of the Mab EGP 13C6-1-1 to the epitopes of Ebola GP.

The DNA sequence of the variable regions of the light chain of Mab EGP 13C6-1-1 is represented in SEQ ID NO:16, and the amino acid sequence is represented in SEQ ID NO:17. For the light chain, the CDRs were identified as located at the following amino acid positions:

24–34: having the amino acid sequence—KASQNVGTAVA (SEQ ID NO:18)

50–56: having the amino acid sequence—SASNRYT (SEQ ID NO:19) and

89–97: having the amino acid sequence—QQYSSYPLT (SEQ ID NO:20).

It is believed that all three CDRs are necessary for effective binding of the Mab EGP13C6-1-1 to the epitopes of Ebola GP. The invention also contemplates monoclonal antibodies having sequences that are at least 90%, and preferably 95%, homologous to the heavy and/or light chain regions described here as SEQ ID NO:11, SEQ ID NO:12, SEQ ID NO:16 and SEQ ID NO:17, and which compete for binding Ebola GP. There can be a 5% variation normally in even the more conserved framework regions, and someone having ordinary skill in this art using known techniques would be able to determine without undue experimentation such homologous, competing monoclonal antibodies. The invention also contemplates monoclonal antibodies that compete with EGP13C6-1-1 for binding to Ebola GP, and which have the above-described CDRs in the appropriate positions as determined by the Kabat system in the light and/or heavy chains.

Specificity is conferred with both heavy and light chains, and not usually with just the heavy or light chain alone; therefore, it is preferred that when this monoclonal antibody is used to detect Ebola in a sample (as described below), or to prevent or treat Ebola infection (as described below), both heavy and light chains are present.

The DNA sequence of the variable regions of the heavy chain of Mab EGP6D8-1-2 is represented in SEQ ID NO:21, and the amino acid sequence is represented in SEQ ID NO:22. For the heavy chain, the CDRs were identified as located at the following amino acid positions:

31–35: having the amino acid sequence—RYWMS (SEQ ID NO:23)

50–65 (includes 52a): having the amino acid sequence—EINPDSSTINYTPSLKD (SEQ ID NO:24)

95–102 (has one deletion): having the amino acid sequence—QGYGYNY (SEQ ID NO:25)

It is believed that all three CDRs are necessary for effective binding of the Mab EGP6D8-1-2 to the epitopes of Ebola GP.

The DNA sequence of the variable regions of the light chain of Mab EGP 6D8-1-2 is represented in SEQ ID NO:26, and the amino acid sequence is represented in SEQ ID NO:27. For the light chain, the CDRs were identified as located at the following amino acid positions:

24–34, includes 27 a–e: having the amino acid sequence RSSQSIVHSNGNTYLE (SEQ ID NO:28)

50–56: having the amino acid sequence KASNRFS (SEQ ID NO:29) and

89–97: having the amino acid sequence LQGSHVPST (SEQ ID NO:30).

It is believed that all three CDRs are necessary for effective binding of the Mab EGP 6D8-1-2 to the epitopes of Ebola GP. The invention also contemplates monoclonal antibodies having sequences that are at least 90%, and preferably 95%, homologous to the heavy and/or light chain regions described here as SEQ ID NO:21, SEQ ID NO:22, SEQ ID NO:26 and SEQ ID NO:27, and which compete for binding Ebola GP. As noted above, there can be a 5% variation normally in even the more conserved framework regions, and someone having ordinary skill in this art using known techniques would be able to determine without undue experimentation such homologous, competing monoclonal antibodies. The invention also contemplates monoclonal antibodies that compete with EGP6D8-1-2 for binding to Ebola GP, and which have the above-described CDRs in the appropriate positions as determined by the Kabat system in the light and/or heavy chains. Specificity generally is conferred with both heavy and light chains, and not usually with just the heavy or light chain alone; therefore, it is preferred that when this monoclonal antibody is used to detect Ebola in a sample (as described below), or to prevent or treat Ebola infection (as described below), both heavy and light chains are present.

The DNA sequence of the variable regions of the heavy chain of Mab EGP 13F6-1-2 is represented in SEQ ID NO:31, and the amino acid sequence is represented in SEQ ID NO:32. For the heavy chain, the CDRs were identified as located at the following amino acid positions:

31–35: having the amino acid sequence SYDMS (SEQ ID NO:33)

50–65: having the amino acid sequence YISRGGGYTYYPDTVKG (SEQ ID NO:34)

95–102, includes 100 a–c,h–k: having the amino acid sequence HIYYGSSHYYAMDY (SEQ ID NO:35) and It is thought that some or all of these three CDRs may not be necessary for effective binding of the Mab EGP13F6-1-2 to the epitopes of Ebola GP because the light chain of this antibody is a lambda x, which has been described as sufficient for binding. Lambda x light chains have an insertion at 27a and an insertion of four amino acids at position 54.

The DNA sequence of the variable regions of the light chain of Mab EGP 13F6-1-2 is represented in SEQ ID NO:36, and the amino acid sequence is represented in SEQ ID NO:37. For the light chain, the CDRs were identified as located at the following amino acid positions:

24–34, includes 27a: having the amino acid sequence TLSRQHSTYTIE (SEQ ID NO:38)

50–56, includes insertion at 54: having the amino acid sequence LKKDGSHSTGD (SEQ ID NO:39) and 89–97, INCLUDES 95a–d: having the amino acid sequence GVGDTIKEQFVYV (SEQ ID NO:40).

It is believed that all three CDRs are necessary, and may be sufficient for effective binding of the Mab EGP 13F6-1-2 to the epitopes of Ebola GP. Consequently, when this monoclonal antibody is used to detect Ebola in a sample (as described below), or to prevent or treat Ebola infection (as described below), the light chain may be used alone, or both heavy and light chains together may be present. The invention also contemplates monoclonal antibodies having sequences that are at least 90%, and preferably 95%, homologous to the heavy and/or light chain regions described here as SEQ ID NO:31, SEQ ID NO:32, SEQ ID NO:36 and SEQ ID NO:37, and which compete for binding Ebola GP. As noted above, there can be a 5% variation normally in even the more conserved framework regions, and someone having ordinary skill in this art using known techniques would be able to determine without undue experimentation such homologous, competing monoclonal antibodies. The invention also contemplates monoclonal antibodies that compete with EGP 13F6-1-2 for binding to Ebola GP, and which have the above-described CDRs in the appropriate positions as determined by the Kabat system in the light and/or heavy chains.

The above-described heavy and light chains for Mab EGP 13C6-1-1, Mab EGP 6D8-1-2, and EGP 13F6-1-2 are particularly useful for detecting Ebola GP in a sample suspected of containing Ebola GP, as well as use as therapeutic and prophylactic agents for treating or preventing Ebola infection in susceptible Ebola-infected subjects.

The present invention also pertains to hybridomas producing antibodies which bind to an epitope of Ebola GP. The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The present invention still further pertains to a method for detecting Ebola GP in a sample suspected of containing Ebola GP. The method includes contacting the sample with an antibody which binds an epitope of Ebola GP, allowing the antibody to bind to Ebola GP to form an immunological complex, detecting the formation of the immunological complex and correlating the presence or absence of the immunological complex with the presence or absence of Ebola GP in the sample. The sample can be biological, environmental or a food sample.

The language "detecting the formation of the immunological complex" is intended to include discovery of the presence or absence of Ebola GP in a sample. The presence or absence of Ebola GP can be detected using an immunoassay. A number of immunoassays used to detect and/or quantitate antigens are well known to those of ordinary skill in the art. See Harlow and Lane, Antibodies: A Laboratory Manual (Cold Spring Harbor Laboratory, New York 1988 555–612). Such immunoassays include antibody capture assays, antigen capture assays, and two-antibody sandwich assays. These assays are commonly used by those of ordinary skill in the art. In an antibody capture assay, the antigen is attached to solid support, and labeled antibody is allowed to bind. After washing, the assay is quantitated by measuring the amount of antibody retained on the solid support. A variation of this assay is a competitive ELISA wherein the antigen is bound to the solid support and two solutions containing antibodies which bind the antigen, for example, serum from an Ebola virus vaccinee and a monoclonal antibody of the present invention, are allowed to compete for binding of the antigen. The amount of monoclonal bound is then measured, and a determination is made as to whether the serum contains anti Ebola GP antibodies. This competitive ELISA can be used to indicate immunity to known protective epitopes in a vaccinee following vaccination.

In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that can bind to the antigen.

These immunoassays typically rely on labeled antigens, antibodies, or secondary reagents for detection. These proteins can be labeled with radioactive compounds, enzymes, biotin, or fluorochromes. Of these, radioactive labeling can be used for almost all types of assays and with most variations. Enzyme-conjugated labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Antibodies useful in these assays include monoclonal antibodies, polyclonal antibodies, and affinity purified polyclonal antibodies. Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al., 1976 (Clin. Chim. Acta 70:1–31), and Schurs, A. H. W. M., et al. 1977 (Clin. Chim Acta 81:1–40). Coupling techniques mentioned in the latter are the glutaraldehyde method, the periodate method, the dimaleimide method, and others, all of which are incorporated by reference herein.

The language "biological sample" is intended to include biological material, e.g. cells, tissues, or biological fluid. By "environmental sample" is meant a sample such as soil and water. Food samples include canned goods, meats, and others.

Yet another aspect of the present invention is a kit for detecting Ebola virus in a biological sample. The kit includes a container holding one or more antibodies which binds an epitope of Ebola GP and instructions for using the antibody for the purpose of binding to Ebola GP to form an immunological complex and detecting the formation of the immunological complex such that the presence or absence of the immunological complex correlates with presence or absence of Ebola virus in the sample. Examples of containers include multiwell plates which allow simultaneous detection of Ebola virus in multiple samples.

As described in greater detail below, the present inventors have isolated five monoclonal antibodies which bind to five epitopes on Ebola GP and display in vitro and/or in vivo Ebola virus protective properties. Significantly, the reactivity of the MAbs is applicable against a broad variety of different wild type and laboratory Ebola strains of different types. Wild type strains include for example Ebola Ivory Coast, Ebola Zaire 1976 (Mayinga isolate), Ebola Zaire 1975, and Ebola Sudan (Boniface). Laboratory strains can be derived from wild type strains and include those which have been passaged or animal adapted strains such as mouse-adapted Ebola.

Given these results, monoclonal antibodies according to the present invention are suitable both as therapeutic and prophylactic agents for treating or preventing Ebola infection in susceptible Ebola-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting Ebola infection. Any active form of the antibody can be administered, including Fab and F(ab')2 fragments. Antibodies of the present invention can be produced in any system, including insect cells, baculovirus expression systems, chickens, rabbits, goats, cows, or plants such as tomato, potato, corn, banana or strawberry.

Methods for the production of antibodies in these systems are known to a person with ordinary skill in the art. Preferably, the antibodies used are compatible with the recipient species such that the immune response to the MAbs does not result in clearance of the MAbs before virus can be controlled, and the induced immune response to the MAbs in the subject does not induce "serum sickness" in the subject. Preferably, the MAbs administered exhibit some secondary functions such as binding to Fc receptors of the subject.

Treatment of individuals having Ebola infection may comprise the administration of a therapeutically effective amount of Ebola antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to Ebola GP, or an antibody capable of protecting against Ebola virus in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use.

In a similar approach, another therapeutic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-GP response (Linthicum, D. S. and Farid, N. R., Anti-Idiotypes, Receptors, and Molecular Mimicry (1988), pp 1–5 and 285–300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof. Alternative protein modification techniques may be used e.g., NH2-acetylation or COOH-terminal amidation, to provide additional means for coupling or fusing the peptide to another protein or peptide molecule or to a support.

The antibodies capable of protecting against Ebola virus are intended to be provided to recipient subjects in an amount sufficient to effect a reduction in the Ebola virus infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in Remington's Pharmaceutical Sciences (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle. Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lacticacid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Administration of the antibodies disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation. The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Cell Lines and Viruses

BHK (ATCC CCL 10), Vero 76 (ATCC CRL 1587), and Vero E6 (ATCC CRL 1586) cell lines were maintained in minimal essential medium with Earle's salts, 10% heat-inactivated fetal bovine serum, and 50 ug/ml gentamicin sulfate. Mouse hybridoma cell lines were maintained in Optimem medium (Life Technologies, Rockville, Md.).

A stock of the Zaire strain of Ebola virus originally isolated from a patient in the 1976 Ebola outbreak (isolate Mayinga) and passaged intracerebrally 3 times in suckling mice and 2 times in Vero cells was adapted to adult mice through serial passage in progressively older suckling mice (Bray et al., J. Infect. Dis. 178, 651–661, 1998). A plaque-purified ninth-mouse-passage isolate which was uniformly lethal for adult mice ("mouse-adapted virus") was propagated in Vero E6 cells, aliquotted, and used in all mouse challenge experiments.

Ebola virus antigens used for characterization of monoclonal antibodies were prepared from the following virus seed stocks that were kindly provided by Dr. Peter Jahrling at USAMRIID: the Zaire 1995 strain of Ebola virus isolated from a patient in the 1995 outbreak and passaged 2 times in Vero E6 cells and 2 times in Vero cells; the Zaire 1976 strain of Ebola virus isolated from a patient in the 1976 Ebola outbreak (isolate Mayinga); the Sudan strain of Ebola virus (isolate Boniface) passaged 1 time in a guinea pig, and 3 times in Vero cells; the Ivory Coast strain of Ebola virus obtained from the Center for Disease Control (CDC #807212) and passaged 4 times in Vero E6 cells and 1 time in Vero cells.

Production of Monoclonal Antibodies

Five BALB/c mice were injected subcutaneously at the base of the neck with 2×106 focus-forming units of Venezuelan equine encephalitis (VEE) virus replicons encoding the glycoprotein (EboGP-VRP) from the Mayinga isolate of the Zaire strain of Ebola virus. EboGP-VRP particles were packaged and purified as described (Pushko et al., 1997 In Vacines 97, pp.253–258. Cold Spring Harbor, N.Y.). Mice received 2 additional subcutaneous injections at one month intervals. ELISA titers to Ebola virus were measured after the third injection and the best two responders received an intravenous injection of 1×107 focus-forming units of Ebola GP replicons (EboGP-VRP) in the tail vein 21 days after the third subcutaneous injection. Three days after the final immunization, spleens were removed and used for fusion to P3X63Ag8:653 myeloma cells as previously described (Stiles et al., Toxicon 29, 1195–1204, 1991). Hybridoma culture supernatants were screened for the presence of antibodies to the Ebola GP by ELISA and by indirect immunofluorescence with fluorescein isothiocyanate (FITC)-conjugated goat anti-mouse antibodies as described below. Positive hybridoma cultures were cloned twice by limiting dilution. Large-scale preparations of MAbs were obtained by culturing hybridoma cell lines in serum-free medium in T150 Integra Celline flasks and purifying the MAbs from the supernatants over Protein G affinity columns (Pharmacia, Piscataway, N.J.). Purified antibodies were dialyzed in PBS and quantitated using a BCA protein assay kit (Pierce, Rockford, Ill.).

Characterization of MAbs

ELISA

Enzyme-linked immunosorbent assays (ELISA) were performed essentially as described (Hevey et al., Virology 239: 206–216, 1997). For screening of MAbs, 96-well PVC plates were coated overnight at 4_C with 0.05 ml of irradiated, sucrose-purified Ebola Zaire 1995 virions (10–20 ug/ml in PBS). For determining the cross-reactivities of the MAbs with other filovirus isolates, PVC plates were coated with either irradiated, sucrose-purified Ebola Zaire 1976 (Mayinga isolate), Ebola Zaire 1995, Ebola Ivory Coast, Ebola Sudan (Boniface). Plates were washed once with PBS containing 0.02% Tween-20 (PBST) and nonspecific binding was blocked by adding 0.25 ml of PBST containing 5% nonfat dry milk (PBSTM) to each well and incubating at room temperature for 1–2 hours. After washing the plates five times with 0.2 ml of PBST, 0.05 ml of undiluted hybridoma culture supernatants or purified MAbs in PBSTM were added to wells containing antigen and plates were incubated for 2 h at room temperature. Bound MAbs were detected using horseradish peroxidase conjugated goat anti-mouse IgA+IgG+IgM (H+L) secondary antibodies and 2,2'-Azinobis-[3-ethylbenzothizoline-6-sulfonic acid] diammonium salt (ABTS) substrate (Kirkegaard and Perry Laboratories, KPL, Gaithersburg, Md.).

Indirect Immunofluroscence Antibody (IFA) Assays

To determine whether the hybridoma cells produced MAbs that recognized either GP or sGP of Ebola virus, Mabs were reacted with Ebola GP-infected BHK cells. BHK cells were infected with EboGP-VRP, or with an irrelevant control replicon expressing the Lassa nucleoprotein, at a multiplicity of infection of 1 to 3 infectious units/cell. Cells were harvested with trypsin 17 h post-infection, washed 2 times in PBS, and diluted to 2×105 cells/ml in PBS. Thirty microliters of the cell suspension was applied to glass spot-slides and the slides were allowed to air dry. Cells were fixed with acetone at −20_C for 15 min and air-dried. Slides were stored at −70_C until needed. Twenty microliters of undiluted hybridoma culture supernatants were added, and the slides were incubated for 30 min at room temperature. Excess antibodies were removed from the cells by washing the slides in PBS for 30 min. Twenty microliters of fluorescein-labeled goat anti-mouse IgA+IgG+IgM (H+L) antibodies (50 ug/ml; KPL) was added to the cells and the slides were incubated for 30 min at room temperature. Excess secondary antibodies were removed from the cells by washing the slides for 30 min in PBS. The PBS was removed from the cells, and one drop of mounting medium (KPL) was added to each of the cell spots. Coverslips were added to the slides and the staining patterns were viewed using a fluorescent microscope.

Metabolic Labeling of Ebola Virus Proteins and Radioimunoprecipitation of Ebola GP Proteins Vero E6 cells (75 cm2 flasks) were infected with the Zaire 1995 strain of Ebola virus at a multiplicity of infection of 1 to 3 plaque-forming units/cell. After 24 hours of infection, the growth medium was removed and cells were starved for 30 minutes in medium lacking methionine and cysteine. To label viral proteins, cells were incubated for 24 hours in MEM medium containing 2% heat-inactivated FBS, 0.1 mCi/ml 35S-labeled methionine and 0.1 mCi/ml 35S-labeled cysteine. The cell medium was harvested and centrifuged to remove cell debris (15 min at 1500×g). Labeled Ebola virions were obtained by pelleting the clarified supernatant over a 20% sucrose cushion (3 h at 36,000 rpm in a SW41 rotor) and suspending the pelleted virions in Zwittergent lysis buffer. Ebola-infected cell lysates were obtained 24 hours after labeling by lysing infected cell monolayers in Zwittergent Lysis buffer.

To immunoprecipitate Ebola GP from EboGP-VRP-infected cells, Vero cells (75 cm2 flasks) were infected with EboGP-VRP at a multiplicity of infection of 1 to 3 infectious units/cell. After 16 h of infection, cells were starved for 30 minutes in medium lacking methionine and cysteine. To label proteins, cells were incubated for 4 hours in MEM medium containing 2% heat-inactivated FBS, 0.1 mCi/ml 35S-labeled methionine and 0.1 mCi/ml 35S-labeled cysteine. Ebola GP mouse MAbs were used to immunoprecipitate Ebola GP proteins from the labeled cell lysates or supernatants.

Western Blot Analysis

Unlabeled Ebola Zaire 1995 virion proteins were resolved on a 10% SDS-polyacrylamide gel and the proteins were transferred to Immobilon-P PVDF membranes. Nonspecific binding sites were blocked by incubating the membranes overnight at 4_C in PBSTM. Purified MAb (10 ug/ml in PBSTM) were added to the membranes for 1 hour at room temperature. The membranes were then incubated with horseradish peroxidase-conjugated goat anti-mouse IgA+IgG+IgM (H+L) secondary antibodies (1 ug/ml in PBSTM) for 1 hour at room temperature, and the ECL Western blot chemiluminescence kit (Amersham) was used to detect bound MAbs.

Isotype Determination

Antibody subclasses were determined by ELISA. Briefly, 96-well plates were coated with anti-IgG, IgA or IgM heavy-chain specific antibodies (100 ng/well, KPL) and incubated with hybridoma culture supernatants. The subtype of the MAb was detected by using anti-IgG1 (Zymed, South San Francisco, Calif.), IgG2a, IgG2b, IgG3 (Cappel, Durham, N.C.), IgM (KPL), or IgA (Sigma, St. Louis, Mo.) heavy-chain specific antibodies conjugated to alkaline phosphatase.

Biotinylation of MAbs and Competitive Binding Assays

MAbs were biotinylated using an EZ-Link_Sulfo-NHS-LC-Biotinylation kit (Pierce, Rockford, Ill.) according to the manufacturer's instructions. Competitive binding between unlabeled and biotin-labeled MAbs was performed by reacting a 20-fold excess of unlabeled MAb and 1 to 200 micrograms of biotin-labeled MAb with sucrose-purified, irradiated Ebola Zaire 1995 virus bound to PVC plates. The results of the competition experiment were evaluated by ELISA. The concentrations of biotinylated MAbs used in the competition assays were previously determined to be in the linear portion of their binding curve to Ebola virus antigen.

In Vitro Plaque-Reduction Neutralization Assay

Plaque assays were performed using confluent Vero-E6 cells. To evaluate the presence of Ebola-neutralizing antibodies, four-fold serial dilutions of MAbs were mixed with 100 pfu of mouse-adapted Ebola virus at 37° C. for 1 h, and used to infect Vero E6 cells. Cells were covered with an agarose overlay (Moe, J. et al. (1981) J. Clin. Microbiol. 13:791–793) and a second overlay containing 5% neutral red solution in PBS or agarose was added 6 days later. Plaques were counted the following day. Endpoint titers were determined to be the last dilution of MAb that reduced the number of plaques by 80% of the control wells.

SPOTS Peptide Analysis.

To identify the protein sequences recognized by the MAbs, 166 peptides from the Ebola virus Zaire glycoprotein sequence were synthesized on membranes. Each peptide was 13 amino acids long and had a 9 amino acid overlap with the preceding and subsequent peptides. Peptides were synthesized directly on SPOTS membranes by Genosys, Inc. Two identical membranes were synthesized. Membranes were washed with methanol and then with PBS-0.02% Tween 20 (PBST), blocked overnight at 4° C. in PBST+5% nonfat dry milk (PBSTM), and rinsed in PBST. Ebola virus-specific MAbs were diluted to 5 micrograms/ml in PBSTM milk. Membranes were incubated with 25 ml of MAb for 1.5 h at room temperature, washed for 15 minutes in PBST and then twice more for 5 minutes each. The secondary antibody (affinity purified, peroxidase-labeled goat anti-mouse IgA+IgM+IgG (H+L), Kirkegaard-Perry Labs, Inc. Catalog Number 074-1807, Lot SM055) was diluted 1:1000 in PBSTM and reacted with the membrane for 1.5 hrs at room temperature. The membrane was washed three times in PBST as described above. Lumi GLO chemiluminescent substrate (Kirkegaard Perry Catalog No. 54-61-00, Lot WD033) was prepared according to manufacturer's instructions and added to the membrane for 1 minute at room temperature. The membrane was exposed to Polaroid film using Amersham's ECL camera for various times. Positive spots were white against a black background. Membranes were reused after stripping. Stripping the membrane was performed by rinsing three times for 10 minutes each in 20 ml of MilliQ water, followed by dimethylformamide, and then twice in 20 ml MilliQ water. Three 10 minute washes in 20 ml regeneration buffer A (8M urea, 1% SDS, 0.1% 2-mercaptoethanol) were followed by three (50% ethanol, 10% acetic acid) and then by two 10 minute washes each in 20 ml methanol followed by PBST. Membranes were then blocked as described above.

Evaluation of MAbs in Mice

Administration of MAbs

To determine the prophylactic benefit of Ebola GP MAbs, purified MAbs or combinations of MAbs were injected intraperitoneally into BALB/c or C57BL/6 mice 24 h prior to challenge with mouse-adapted Ebola Zaire virus. For examination of therapeutic effects of MAbs, 100 micrograms of purified antibody, or various concentrations of combined MAbs, were injected intraperitoneally into BALB/c and C57BL/6 mice either 1, 2, or 3 days after challenge with mouse-adapted Ebola Zaire virus. All antibodies were diluted in sterile PBS and 0.2 ml was injected into each mouse.

Ebola Infection of Mice

Mice were transferred to a BSL-4 containment area and challenged by intraperitoneal inoculation of 10 pfu of mouse-adapted Ebola Zaire 1976 virus (approximately 300 times the dose lethal for 50% of adult mice). Virus was diluted in EMEM medium without FBS. Animals were monitored for morbidity and mortality for 28 days post-infection.

Production of EboGP-VRP

The GP gene of Ebola Zaire was previously sequenced by Sanchez et al. (1993, supra) and has been deposited in GenBank (accession number L11365). A plasmid encoding the VEE replicon vector containing a unique ClaI site downstream from the 26S promoter was described previously (Davis, N. L. et al., (1996) J. Virol. 70, 3781–3787; Pushko, P. et al. (1997) Virology 239, 389–401). The Ebola GP gene from the Ebola Zaire 1976 virus were derived from PS64-based plasmid (Sanchez, A. et al. (1989) Virology 170, 81–91; Sanchez, A. et al. (1993) Virus Res. 29, 215–240). From this plasmid, the BamHI-KpnI (2.4 kb) fragment containing the GP gene was subcloned into a shuttle vector that had been digested with BamHI and EcoRI (Davis et al. (1996) supra; Grieder, F. B. et al. (1995) Virology 206, 994–1006). For cloning of the GP gene, overhanging ends produced by KpnI (in the GP fragment) and EcoRI (in the shuttle vector) were made blunt by incubation with T4 DNA polymerase according to methods known in the art. From the shuttle vector, the GP gene was subcloned as ClaI-fragments into the ClaI site of the replicon clone, resulting in a plasmid encoding the GP gene in place of the VEE structural protein genes downstream from the VEE 26S promoter, resulting in the replicon construct, VRepEboGP.

The Ebola virus GP gene cloned into the VEE replicon was sequenced. Changes in the DNA sequence relative to the sequence published by Sanchez et al. (1993) are described relative to the nucleotide (nt) sequence number from GenBank (accession number L11365).

The nucleotide sequence we obtained for Ebola virus GP (SEQ ID NO:1) differed from the GenBank sequence by a transition from A to G at nt 8023. This resulted in a change in the amino acid sequence from Ile to Val at position 662 (SEQ ID NO: 2).

Transfection of the replicon construct, VRepEboGP along with helper RNAs containing sequences necessary for packaging of the viral replicon transcripts will result in the production of virus-like particles containing replicon RNAs, such as EboGP-VRP. These packaged replicons will infect host cells and initiate a single round of replication resulting in the expression of the Ebola proteins in said infected cells.

EXAMPLE 1

Production and Characterization of Ebola GP MAbs

To obtain MAbs specific for the glycoprotein of Ebola virus, mice were vaccinated with VEE virus replicon particles (VRP) that express Ebola GP (EboGP-VRP). Spleen cells from two mice that were vaccinated with with EboGP-VRP were pooled and fused with P3X63Ag8:653 myeloma cells as described in Methods. In order to detect hybridomas producing antibodies that reacted with the GP of Ebola virus, 1,738 hybridoma supernatants were screened by ELISA for their ability to react with Ebola Zaire virion proteins and by indirect immunofluorescence assay (IFA) for their ability to react with BHK cells infected with EboGP-VRP. The initial screening by ELISA and IFA resulted in 616 positive cultures. Forty of these cultures were chosen for further analysis and were cloned twice by limited dilution. Twenty-seven of the hybridoma cultures continued to react specifically with the Ebola GP throughout the cloning process. The other hybridoma cultures were either lost in the cloning process or produced antibodies that reacted with cellular proteins. Isotype analysis of the MAbs produced by the 27 hybridoma cultures demonstrated that 6 were of the IgG1 subclass, 17 were of the IgG2a subclass, 2 were of the IgG2b subclass, 1 was of the IgG3 subclass, and 1 was an IgA antibody. All of the MAbs produced by these hybridoma cultures reacted with Ebola GP by IFA and 23 of the 27 MAbs reacted with Ebola virions by ELISA. These hybridoma cell lines were cultured in serum-free medium (Life Technologies, Grand Island, N.Y.) in Integra Celline flasks (Integra Biosciences, Inc., Ijamsville, Md.). The IgG MAbs were purified from the supernatants on Protein G affinity columns (Amersham Pharmacia, Piscataway, N.J.), dialyzed in phosphate-buffered saline, and measured using the BCA protein assay (Pierce, Rockford, Ill.).

EXAMPLE 2

Protective Efficacy of Ebola GP MAbs In Vivo

In order to determine the protective efficacy of the Ebola GP MAbs, purified MAbs were evaluated for their ability to protect mice from a lethal Ebola challenge (Table 3). In addition, competitive binding assays were performed to determine if the MAbs were recognizing the same epitope or unique epitopes on the Ebola GP (Example 3, Table 4). Fourteen of the MAbs tested in competition assays reacted with 5 different epitopes (Table 5). Ten of these 14 MAbs protected both BALB/c and C57BL/6 mice from a lethal challenge with mouse-adapted Ebola Zaire virus when 100 ug of purified MAb was administered 24 hours before challenge (Tables 3 and 5), demonstrating that antibodies that bind to any one of these Ebola GP epitopes can protect against lethal challenge.

To determine the effective dose of the protective MAbs, BALB/c mice were injected with either 50 ug, 25 ug, or 12.5 ug of purified Ebola GP MAbs 24 h prior to challenge with a lethal dose of mouse-adapted Ebola Zaire virus. For all of the MAbs examined, protection from Ebola challenge decreased when the MAb dose was lowered to 50 or 25 ug (Table 3). No protection was observed for any of the mice that received 12.5 ug of MAb (data not shown). For the most effective MAbs, the amount required for protection was within an achievable human therapeutic dose of 3–5 mg/kg.

To determine if the MAbs could be used therapeutically to treat mice that had already been infected with the Ebola virus, 100 ug of purified MAbs were injected into BALB/c or C57BL/6 mice either 1, 2, or 3 days after a lethal challenge with mouse-adapted Ebola Zaire virus. All of the MAbs that demonstrated protective efficacy when administered 1 day prior to challenge were also effective therape challenge (Table 3). Some of the MAbs were effective even when administered up to 2 days after challenge (Table 3), after significant viral replication had occurred (M. Bray et al., J. Infect. Dis. 178, 651 (1998)). None of the tested MAbs were protective when 100 ug was administered 3 days after challenge (data not shown), when there are high viral titers and possibly irreversible damage of cells and organs.

TABLE 3

Protective Efficacy of Ebola GP Monoclonal Antibodies.

| Competition Group | MAb Designation | Day MAb Administered[1] | BALB/c S/T[2] (100 ug) | BALB/c S/T[2] (50 ug) | BALB/c S/T[2] (25 ug) | C57BL/6 S/T[2] (100 ug) |
|---|---|---|---|---|---|---|
| 1 | 13F6 | −1 | 10/10 | 7/10 | 6/10 | 9/10 |
| | (IgG2a) | +1 | 10/10 | — | — | 9/10 |
| | | +2 | 3/10 | — | — | 2/10 |
| 2 | 6D8 | −1 | 10/10 | 6/10 | 3/10 | 9/10 |
| | (IgG2a) | +1 | 10/10 | — | — | 9/10 |
| | | +2 | 6/10 | — | — | 5/10 |
| 3 | 12B5 | −1 | 6/10 | 2/10 | 0/10 | 6/10 |
| | (IgG1) | +1 | 8/10 | — | — | 6/10 |
| | | +2 | 1/10 | — | — | 1/10 |
| 4 | 13C6 | −1 | 10/10 | 7/10 | 3/10 | 9/10 |
| | (IgG2a) | +1 | 10/10 | — | — | 10/10 |
| | | +2 | 8/10 | — | — | 9/10 |
| 5 | 6D3 | −1 | 9/10 | 6/10 | 2/10 | 8/10 |
| | (IgG2a) | +1 | 10/10 | — | — | 9/10 |
| | | +2 | 9/10 | — | — | 8/10 |
| — | Diluent | −1 | 0/10 | — | — | 0/10 |
| | (PBS) | +1 | 0/10 | — | — | 0/10 |
| | | +2 | 0/10 | — | — | 0/10 |

[1]Groups of five mice per experiment were injected intraperitoneally with either 100, 50, or 25 ug of MAb in phosphate-buffered saline (PBS) 1 day before (−1), or 1 or 2 days after (+1, +2), challenge with 300 times the dose lethal for 50% of adult mice (10 plaque-forming units) of mouse-adapted Ebola Zaire virus.
[2]S/T, Number of mice that survived challenge/total number challenged.

EXAMPLE 3

Competitive Binding of Ebola GP MAbs

This study identified protective GP-specific MAbs that were classified into five groups on the basis of competitive binding assays. One protective MAb from each of these five different competition groups was chosen for further characterization and was submitted to ATCC as a representative of the competition group. Competitive binding between biotinylated and unlabeled MAbs for the GP of the Ebola Zaire 1995 virus was evaluated by ELISA. The results of the binding assays for the prototypical protective MAb from each competition group are depicted in Table 4. Except for one instance of one-way competition (between the group 4 and 5 MAbs), competition between labeled and unlabeled MAbs was reciprocal.

TABLE 4

Competitive Binding of Ebola GP MAbs

| | Competing Unlabeled MAb | | | | |
|---|---|---|---|---|---|
| Biotinylated MAb | 13F6 | 6D8 | 12B5 | 13C6 | 6D3 |
| 13F6 | 0.3 | 0.8 | 0.5 | 1.0 | 1.2 |
| 6D8 | 0.6 | 0.2 | 0.6 | 0.6 | 0.7 |
| 12B5 | 0.3 | 0.3 | 0.1 | 0.2 | 0.3 |
| 13C6 | 0.6 | 0.7 | 0.6 | 0.1 | 0.5 |
| 6D3 | 0.5 | 0.6 | 0.6 | 0.1 | 0.2 |

Nonprotective MAbs were identified that bound competitively with protective MAbs in groups 1, 4 and 5 (Table 5). All of the antibodies that were completely protective were of the IgG2a subclass, whereas the competing nonprotective MAbs in groups 1 and 4 were of the IgG1 or IgG3 subclasses. Furthermore, the group 3 MAb (12B5), which was only partially protective, was IgG1. Thus, antibody subclass may be an important factor in protection. Murine IgG2a binds complement more effectively than IgG1 or IgG3 and varies in its affinity for different Fe receptors (H. Waldmann, Ann. Rev. Immunol. 7, 407 (1989)). The subclass of the antibody may therefore affect the ability of the MAbs to resolve Ebola infections, for example by lysing infected cells through the classical complement pathway or by binding Fc receptors on cellular effectors of antibody-dependent-cell-mediated cytotoxicity.

TABLE 5

Competition Groups of Ebola GP MAbs

| Competition Group | MAb Designation | MAb Isotype | Protection In Mice |
|---|---|---|---|
| 1 | 13F6 | IgG2a | Yes |
| 1 | 6E3 | IgG1 | No |
| 2 | 6D8 | IgG2a | Yes |
| 2 | 7E10 | IgG2a | Yes |
| 2 | 17E11 | IgG2a | Yes |
| 3 | 12B5 | IgG1 | Yes |
| 4 | 13C6 | IgG2a | Yes |
| 4 | 11H12 | IgG2a | Yes |
| 4 | 9H6 | IgG2a | Yes |
| 4 | 1G8 | IgG2a | Yes |
| 4 | 12E12 | IgG3 | No |
| 5 | 6D3 | IgG2a | Yes |
| 5 | 8C10 | IgG2a | No |
| 5 | 3H8 | IgG2a | No |

Alternatively, the affinity of an antibody for its epitope, possibly influenced by post-translational modifications such as glycosylation, may be an important determinant of protective efficacy. For instance, although group 5 consisted of three IgG2a MAbs, only 6D3 (Table 5) was protective. This MAb bound to Ebola virus at 10-fold lower concentrations than the two nonprotective MAbs (data not shown). In addition, the protective MAb in competition group 1 was more effective than the nonprotective MAb in competition assays (data not shown), suggesting that protective MAbs may have higher affinities for the epitope than nonprotective MAbs.

EXAMPLE 4

Epitopes Bound by Ebola GP MAbs

To further analyze the binding characteristics of the protective MAbs, MAbs were examined by radioimmunoprecipitation, western blot analysis, and peptide-binding assays. MAbs in competition groups 1, 2, and 3 immunoprecipitated GP, but not sGP, from supernatants of cell cultures infected with either Ebola Zaire virus or EboGP-VRPs (FIG. 2), and reacted only with GP1 in western blots (data not shown). The sequences bound by these MAbs were identified by means of synthetic peptides immobilized on membranes and were confirmed with soluble peptides in competition ELISAs (Table 2). These protective MAbs bound linear epitopes within a region of 106 amino acids in the C-terminal portion of GP1. This region is poorly conserved among Ebola viruses and is not shared with sGP. The epitopes bound by MAbs in competition groups 1 and 2 are separated by only three amino acids (Table 2).

In contrast, MAbs in competition groups 4 and 5 immunoprecipitated both GP and sGP from supernatants of infected cells (FIG. 2) but did not bind GP on western blots under reducing conditions or react with any of the synthetic Ebola GP peptides immobilized on membranes (data not shown). These epitopes are therefore discontinuous or require a specific conformation for binding, and are located within the N-terminal 295 amino acids that are identical between sGP and GP1.

EXAMPLE 5

Cross-Reactivity of MAbs with Ebola Virus Subtypes

All of the MAbs in this report were generated against the Zaire strain of the Ebola virus. To determine if the MAbs cross-react with the GP of other Ebola strains that are human pathogens, the reactivities of the MAbs with the Zaire 1976, Zaire 1995, Ivory Coast, and Sudan isolates of Ebola virus were compared by ELISA. The Reston strain of the Ebola virus has not been demonstrated to be a human pathogen and was therefore not tested in this report.

When the MAbs were tested for reactivity with the Ebola viruses that are human pathogens, MAbs in competition groups 1, 2, and 3 bound to the two Zaire isolates that have caused the most devastating outbreaks, but did not bind to the Ivory Coast or Sudan viruses (Table 2). All of the MAbs in competition groups 4 and 5 bound to the Ebola Zaire and Ivory Coast viruses. Furthermore, MAbs in competition group 4, but not group 5, also bound to Ebola Sudan (Table 2). These results suggest that it is possible to elicit by vaccination, or produce for therapeutic use, antibodies protective against all Ebola viruses that are pathogenic for humans.

EXAMPLE 6

In Vitro Neutralization of Ebola Virus by Ebola GP MAbs

In order to determine if the protective MAbs were able to neutralize Ebola virus in vitro, purified MAbs were evaluated for their ability to inhibit plaque formation by Ebola virus. None of the protective MAbs inhibited plaque formation in the absence of complement (Table 6). In the presence of complement, only MAbs in competition groups 2 and 4 neutralized the virus (80% at 6.25 ug/ml, Table 6). MAb 12B5 (competition group 3) did not reduce the number of plaques, but did reduce plaque size (Table 6), suggesting that it restricted subsequent infection of adjacent cells. These results demonstrated that the ability of the MAbs to inhibit plaque formation by Ebola virus, a standard assay of virus neutralization, did not always predict their protective efficacy.

TABLE 6

In Vitro Neutralization Activity of Ebola GP MAbs.

| MAb Designation | Competition Group | Neutralization w/Complement | Neutralization w/o Complement |
|---|---|---|---|
| 13F6 | 1 | None | None |
| 6D8 | 2 | 6.25 ug/ml | None |
| 12B5 | 3 | None* | None* |
| 13C6 | 4 | 6.25 ug/ml | None |
| 6D3 | 5 | None | None |

*Plaque size was reduced (pinpoint plaques) compared with control plaques. Plaque assays were performed using confluent Vero-E6 cells. To evaluate the presence of Ebola-neutralizing antibodies, four-fold serial dilutions of MAbs (starting at 100 æg/ml) were mixed with 100 pfu of mouse-adapted Ebola virus at 37øC for 1 h, and used to infect Vero E6 cells. Cells were covered with an agarose overlay (Moe, J. et al. (1981) J. Clin. Microbiol. 13:791–793) and a second overlay containing 5% neutral red solution in PBS or agarose was added 6 days later. Plaques were counted the following day. In some experiments, guinea pig complement (5% final concentration) was added to facilitate antibody-complement lysis of infected cells. Endpoint titers were determined to be the last dilution of MAb that reduced the number of plaques by 80% compared with the control wells.

EXAMPLE 7

Combinations of MAbs Can Reduce the Effective Dose Required for In Vivo Protection from Ebola Virus Table 3 demonstrated that MAbs recognizing single epitopes on the Ebola GP were capable of protecting mice from lethal Ebola challenge when 100 ug of Mab was administered either 1 day before or up to 2 days after receiving a lethal dose of Ebola virus. To determine if combinations of MAbs from different competition groups could reduce the effective dose required for protection, MAbs from 3 to 5 different competition groups were mixed and evaluated for their ability to protect BALB/c mice from a lethal challenge with mouse-adapted Ebola Zaire virus. The concentrations of MAbs chosen for these studies were below the concentrations at which the individual MAbs were able to protect all of the mice from death.

Administration of 37.5 ug of a combination of 3 different MAbs (12.5 ug of MAb 13F6, 12.5 ug of MAb 6D8, and 12.5 ug of MAb 13C6) one day prior to Ebola challenge was able to protect 4/5 mice from lethal disease (Table 7A). When the same 3 MAbs were administered at concentrations of either 25 ug or 50 ug of each MAb/mouse (for a total of 75 ug or 150 ug of MAb/mouse, respectively), 100% of the mice were protected from lethal challenge. Therefore, prophylactic administration of a combination of MAbs that recognize different epitopes on the Ebola GP is more efficient than single MAbs at protecting against lethal challenge.

To determine if combinations of MAbs were also effective therapeutically, groups of 5 BALB/c mice were injected with various combinations of MAbs 2 days after a lethal challenge with mouse-adapted Ebola Zaire virus. Combinations of MAbs 13F6, 6D8, and 13C6 were able to protect 4/5 mice when administered at a concentration of 25 ug or 50 ug of each MAb/mouse (Table 7B). When combinations of MAbs 13F6, 6D8, 12B5, 13C6, and 6D3, representing the 5 different competition groups for protective Ebola GP MAbs, were administered at a concentration of either 12.5 ug or 25 ug of each MAb/mouse 2 days after Ebola challenge, all of the mice survived (Table 7B). Therefore, combinations of MAbs which recognize different epitopes on the Ebola GP are effective both prophylactically when administered one day prior to Ebola challenge and therapeutically when administered 2 days after Ebola challenge when significant viral replication has already occurred in the host.

TABLE 7

Protective Efficacy of Combinations of Ebola GP Monoclonal Antibodies

| Mabs Administered | MAb Dose[1] (ug) | Survivors/ Total | MDD[2] |
|---|---|---|---|
| A. Prophylactic Administration (1 Day Prior to Challenge): | | | |
| 13F6, 6D8, and 13C6 | 12.5 of each (37.5 total) | 4/5 | 9* |
| 13F6, 6D8, and 13C6 | 25 of each (75 total) | 5/5 | — |
| 13F6, 6D8, and 13C6 | 50 of each (150 total) | 5/5 | — |
| None (PBS) | — | 0/5 | 6.6 ± 2.0 |
| B. Therapeutic Administration (Day 2 Post-Challenge): | | | |
| 13F6, 6D8, and 13C6 | 25 of each (75 total) | 4/5 | 6* |
| 13F6, 6D8, and 13C6 | 50 of each (150 total) | 4/5 | 7* |
| 13F6, 6D8, 12B5, 13C6 and 6D3 | 12.5 of each (62.5 total) | 5/5 | — |
| 13F6, 6D8, 12B5, 13C6 and 6D3 | 25 of each (125 total) | 5/5 | — |

[1]MAbs were administered intraperitoneally into BALB/c mice either 1 day before or 2 days after challenge with mouse-adapted Ebola Zaire virus.
[2]MDD, Mean Day of Death
*n = 1

This report thus demonstrates that antibodies are a feasible option for the design of safe and standardized treatments for Ebola infections. However, antibody specificity and the ability to neutralize the Ebola virus in vitro cannot be used as sole predictors of protective efficacy. Protection may depend on the proper specificity, isotype, and/or affinity of the antibody.

EXAMPLE 8

Successful Use of Monoclonal Antibodies in Guinea Pigs

Tests were also run to determine whether the Mabs were useful in guinea pigs. To reduce the chance of death due to antibody-escape mutants, three of the protective Mabs (13F6-1-2, 13C6-1-1 and 6D8-1-2) were pooled and administered to strain 13 guinea pigs at 50 mg/kg. Two of three guinea pigs survived challenge with 1000 pfu of the guinea pig-adapted virus, indicating that the murine Mabs are efficacious in heterologous species. All three control animals died after challenge. The demonstration that the Mabs protected a higher-order species suggests they may be useful for treating other species, including humans, if appropriately formulated.

EXAMPLE 9

Humanizing the Monoclonal Antibodies

To 'humanize' the Mabs to be able to safely administer them to humans with a reduced chance of rejection as foreign proteins, it is necessary to sequence the variable regions of the Mabs so that the important regions involved in binding can be retained in the "humanized" product. To determine the sequences of the heavy and light chain-variable regions of Mab EGP 13C6-1-1, Mab EGP 6D8-1-2 and Mab EGP 13F6-1-2, the following protocol was carried out. Cellular RNA was first extracted from the hybridoma cells with Trizol (Life Technologies Cat. No. 15596-026). First strand cDNA was synthesized according to manufacturer's recommendations using either a Novagen kit (Catalog No. 69001-3) or an Invitrogen kit (Cat. No. 11904-018) and primers for mouse heavy and light chains obtained from Novagen (Cat. No. 69831-3). PCR amplification was performed using the 5' and 3' primers from the Novagen kit and Expand High Fidelity enzyme (Boehringer Mannheim). PCR products were run on 2% agarose gels and purified for sequencing reactions.

Sequencing reactions determined that EGP 13F6-1-2 uses a lambda light chain whereas EGP 6D8-1-2 and EGP 13C6-1-1 use the more common kappa chain. The consensus sequences for the EGP Mab heavy and light chains are indicated below. The underlined regions indicate primer sequences, and the start codon is in boldface type.

The EGP 13C6-1-1 IgG $V_H$ heavy chain amplified with D primers is indicated in SEQ ID:NO 11 (DNA sequence), and the translated variable and J regions are indicated in SEQ ID:NO 12 (amino acid sequence). The EGP13C6-1-1 Kappa light chain amplified with D primers is indicated in SEQ ID:NO 16 (DNA sequence), and the translated sequence is indicated in SEQ ID:NO 17 (amino acid sequence).

The EGP 6D8-1-2 IgG $V_H$ heavy chain amplified with F primers is indicated in SEQ ID:NO 21 (DNA sequence), and the translated sequence is indicated in SEQ ID:NO 22 (amino acid sequence). The EGP 6D8-1-2 Kappa light chain amplified with G primers is indicated in SEQ ID:NO 26 (DNA sequence), and the translated sequence is indicated in SEQ ID:NO 27 (amino acid sequence).

The EGP 13F6-1-2 IgG $V_H$ heavy chain amplified with A primer is indicated in SEQ ID:NO 31 (DNA sequence), and the translated sequence is indicated in SEQ ID:NO 32 (amino acid sequence). The EGP 13F6-1-2 IgG $V_{LAMBDA}$ light chain amplified with 5' lambda primers is indicated in SEQ ID:NO 36 (DNA sequence), and the translated sequence is indicated in SEQ ID:NO 37 (amino acid sequence).

Using the numbering system of Kabat, the complementarity determining regions for each Mab were identified and the sequences listed. It is understood in the art that these regions form a 3-dimensional structure that interacts with an epitope on the antigen, and that this combination will differ for each clone. It is the 3-dimensional structure formed by the complementarity-determining regions that needs to be preserved in the "humanized" product. The complementarity-determining regions for Mab 13C6-1-1 are shown as SEQ ID 13–15 and 18–20, for Mab 6D8-1-2 as SEQ ID 23–25 and 28–30 for Mab 13F6-1-2 as SEQ ID 33–35 and 38–40.

Using techniques currently known, these CDRs may then be generated into a backbone that is a human MAb with human framework and constant regions. Those having ordinary skill in the art of molecular biology could clone the entire variable regions onto human constant region genes to produce a chimeric mouse-human antibody. To reduce the amount of mouse sequence retained in the product (which can induce human anti-mouse responses) the CDRs can be molecularly cloned into an otherwise completely human antibody sequence. This produces a "humanized" Mab which retains only the mouse CDR sequences. Alternatively, one could use a mouse strain that has been genetically altered to produce fully human antibodies to functionally reproduce the Mabs described in this application in human form. Such mice can be obtained, for example, from Abgenix or Medarex. The use of phage display libraries, in which Mabs are derived from a human repertoire, is another way to produce the Mabs described herein in a fully human form. Screening the human Mabs for reactivity with the Ebola GP sequences SEQ ID:Nos 5, 7 and/or 9 or by competition ELISA with the mouse Mabs described in this disclosure provides a quick, easy method of identifying Mabs with the same functional properties as ours.

All references cited hereinabove are incorporated by reference in their entirety.

What is claimed is:

1. An isolated monoclonal antibody which binds Ebola virus GP, which monoclonal antibody consists of a heavy chain variable region encoded by the DNA sequence SEQ ID NO:21.

2. An isolated monoclonal antibody which binds Ebola virus GP, which monoclonal antibody consists of a light chain variable region encoded by the DNA sequence SEQ ID NO:26.

3. An isolated monoclonal antibody which binds Ebola virus GP, which monoclonal antibody consists of a heavy chain variable region encoded by the DNA sequence SEQ ID NO:21 and a light chain variable region encoded by the DNA sequence encoded by the DNA sequence SEQ ID NO:26.

4. An immunogenic composition comprising a monoclonal antibody which binds Ebola virus GP, which monoclonal antibody consists of a heavy chain variable region encoded by the DNA sequence SEQ ID NO:21, and a pharmaceutically acceptable carrier.

5. An immunogenic composition comprising a monochonal antibody which binds Ebola virus GP, which monoclonal antibody consists of a light chain variable region encoded by the DNA sequence SEQ ID NO:26, and a pharmaceutically acceptable carrier.

6. An immunogenic composition comprising a monoclonal antibody which binds Ebola virus GP, which monoclonal antibody consists of a heavy chain variable region encoded by the DNA sequence SEQ ID NO:21 and a light chain variable region encoded by the DNA sequence SEQ ID NO:26, and a pharmaceutically acceptable carrier.

* * * * *